(12) United States Patent
Masquelier et al.

(10) Patent No.: US 11,135,584 B2
(45) Date of Patent: *Oct. 5, 2021

(54) INSTRUMENT SYSTEMS FOR INTEGRATED SAMPLE PROCESSING

(71) Applicant: 10X Genomics, Inc., Pleasanton, CA (US)

(72) Inventors: Donald A. Masquelier, Tracy, CA (US); Benjamin Hindson, Pleasanton, CA (US); Kevin Ness, Pleasanton, CA (US); Rajiv Bharadwaj, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 271 days.

This patent is subject to a terminal disclaimer.

(21) Appl. No.: 16/274,134

(22) Filed: Feb. 12, 2019

(65) Prior Publication Data

US 2019/0329245 A1 Oct. 31, 2019

Related U.S. Application Data

(63) Continuation of application No. 15/958,391, filed on Apr. 20, 2018, now Pat. No. 10,245,587, which is a (Continued)

(51) Int. Cl.
*B01L 3/00* (2006.01)
*F16K 99/00* (2006.01)
(Continued)

(52) U.S. Cl.
CPC ........... *B01L 3/50273* (2013.01); *B01L 9/527* (2013.01); *C12Q 1/6874* (2013.01);
(Continued)

(58) Field of Classification Search
CPC ................ B01L 3/50273; B01L 9/527; B01L 2200/027; B01L 2200/0673;
(Continued)

(56) References Cited

U.S. PATENT DOCUMENTS

| 2,797,149 A | 6/1957 | Skeggs |
| 3,047,367 A | 7/1962 | Kessler |

(Continued)

FOREIGN PATENT DOCUMENTS

| CN | 102292455 A | 12/2011 |
| CN | 103202812 A | 7/2013 |

(Continued)

OTHER PUBLICATIONS

10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.

(Continued)

*Primary Examiner* — Michael L Hobbs
(74) *Attorney, Agent, or Firm* — Clark & Elbing LLP

(57) ABSTRACT

An integrated system for processing and preparing samples for analysis may include a microfluidic device including a plurality of parallel channel networks for partitioning the samples including various fluids, and connected to a plurality of inlet and outlet reservoirs, at least a portion of the fluids comprising reagents, a holder including a closeable lid hingedly coupled thereto, in which in a closed configuration, the lid secures the microfluidic device in the holder, and in an open configuration, the lid is a stand orienting the microfluidic device at a desired angle to facilitate recovery of partitions or droplets from the partitioned samples generated within the microfluidic device, and an instrument configured to receive the holder and apply a pressure dif- (Continued)

ferential between the plurality of inlet and outlet reservoirs to drive fluid movement within the channel networks.

21 Claims, 10 Drawing Sheets

Related U.S. Application Data continuation of application No. 14/934,044, filed on Nov. 5, 2015, now Pat. No. 9,975,122.

(60) Provisional application No. 62/075,653, filed on Nov. 5, 2014.

(51) Int. Cl.
*B01L 9/00* (2006.01)
*C12Q 1/6874* (2018.01)

(52) U.S. Cl.
CPC ..... *F16K 99/0057* (2013.01); *B01L 2200/027* (2013.01); *B01L 2200/0673* (2013.01); *B01L 2200/10* (2013.01); *B01L 2300/043* (2013.01); *B01L 2300/0609* (2013.01); *B01L 2300/0636* (2013.01); *B01L 2300/0864* (2013.01); *B01L 2300/10* (2013.01); *B01L 2300/14* (2013.01); *B01L 2300/18* (2013.01); *B01L 2400/0487* (2013.01); *B01L 2400/0605* (2013.01); *F16K 2099/0084* (2013.01)

(58) Field of Classification Search
CPC .......... B01L 2200/10; B01L 2300/043; B01L 2300/0636; B01L 2300/0864; B01L 2300/0609; B01L 2300/10; B01L 2300/14; B01L 2300/18; B01L 2400/0605; B01L 2400/0487; C12Q 1/6874; F61K 99/0057; F61K 2099/0084
See application file for complete search history.

(56) References Cited

U.S. PATENT DOCUMENTS

| | | |
|---|---|---|
| 3,479,141 A | 11/1969 | William et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer et al. |
| 5,618,711 A | 4/1997 | Gelfand et al. |
| 5,658,548 A | 8/1997 | Padhye et al. |
| 5,695,940 A | 12/1997 | Drmanac et al. |
| 5,700,642 A | 12/1997 | Monforte et al. |
| 5,705,628 A | 1/1998 | Hawkins et al. |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,989,402 A | 11/1999 | Chow et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,281,254 B1 | 8/2001 | Nakajima et al. |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,481,453 B1 | 11/2002 | O'Connor et al. |
| 6,485,944 B1 | 11/2002 | Church et al. |
| 6,492,118 B1 | 12/2002 | Abrams et al. |
| 6,503,757 B1 | 1/2003 | Chow et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |

(56) References Cited

U.S. PATENT DOCUMENTS

| | | |
|---|---|---|
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,943,671 B2 | 5/2011 | Herminghaus et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoj et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,089,844 B2 | 7/2015 | Hiddessen et al. |
| 9,102,980 B2 | 8/2015 | Brenner et al. |
| 9,126,160 B2 | 9/2015 | Ness et al. |
| 9,133,009 B2 | 9/2015 | Baroud et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,636,682 B2 | 5/2017 | Hiddessen et al. |
| 9,637,799 B2 | 5/2017 | Fan et al. |
| 9,644,204 B2 | 5/2017 | Hindson et al. |
| 9,649,635 B2 | 5/2017 | Hiddessen et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 9,975,122 B2 * | 5/2018 | Masquelier ......... F16K 99/0057 |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,137,449 B2 | 11/2018 | Bharadwaj et al. |
| 10,150,117 B2 | 12/2018 | Bharadwaj et al. |
| 10,221,442 B2 | 3/2019 | Hindson et al. |
| 10,245,587 B2 * | 4/2019 | Masquelier ......... C12Q 1/6874 |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0052460 A1 | 12/2001 | Chien et al. |
| 2001/0053519 A1 | 12/2001 | Fodor et al. |
| 2002/0001856 A1 | 1/2002 | Chow et al. |
| 2002/0003001 A1 | 1/2002 | Weigl et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2002/0182118 A1 | 12/2002 | Perry |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027203 A1 | 2/2003 | Fields |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |

(56) References Cited

U.S. PATENT DOCUMENTS

| | | |
|---|---|---|
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0021068 A1 | 2/2004 | Staats |
| 2004/0040851 A1 | 3/2004 | Karger et al. |
| 2004/0063138 A1 | 4/2004 | McGinnis et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0195728 A1 | 10/2004 | Slomski et al. |
| 2004/0214175 A9 | 10/2004 | McKernan et al. |
| 2004/0224331 A1 | 11/2004 | Cantor et al. |
| 2004/0228770 A1 | 11/2004 | Gandhi et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0266582 A1 | 12/2005 | Modlin et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0094108 A1 | 5/2006 | Yoder et al. |
| 2006/0153924 A1 | 7/2006 | Griffiths et al. |
| 2006/0163070 A1 | 7/2006 | Boronkay et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0031829 A1 | 2/2007 | Yasuno et al. |
| 2007/0039866 A1 | 2/2007 | Schroeder et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0242111 A1 | 10/2007 | Pamula et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0124726 A1 | 5/2008 | Monforte |
| 2008/0138878 A1 | 6/2008 | Kubu et al. |
| 2008/0166720 A1 | 7/2008 | Hsieh et al. |
| 2008/0213766 A1 | 9/2008 | Brown et al. |
| 2008/0228268 A1 | 9/2008 | Shannon et al. |
| 2008/0230386 A1 | 9/2008 | Srinivasan et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0208548 A1 | 8/2009 | Mason et al. |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2009/0311713 A1 | 12/2009 | Pollack et al. |
| 2009/0320930 A1 | 12/2009 | Zeng et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0029014 A1 | 2/2010 | Wang |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva et al. |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0046243 A1 | 2/2011 | Ito et al. |

(56) References Cited

U.S. PATENT DOCUMENTS

| | | |
|---|---|---|
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0297493 A1 | 11/2012 | Cooper et al. |
| 2012/0309002 A1 | 12/2012 | Link |
| 2012/0316074 A1 | 12/2012 | Saxonov et al. |
| 2012/0328488 A1 | 12/2012 | Puntambekar et al. |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum |
| 2013/0274117 A1 | 10/2013 | Church et al. |
| 2013/0293246 A1 | 11/2013 | Pollack et al. |
| 2013/0296173 A1 | 11/2013 | Callow et al. |
| 2013/0343317 A1 | 12/2013 | Etemad et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev et al. |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0258543 A1 | 9/2015 | Baroud et al. |
| 2015/0259736 A1 | 9/2015 | Steemers et al. |
| 2015/0267191 A1 | 9/2015 | Steelman et al. |
| 2015/0267246 A1 | 9/2015 | Baroud et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0123858 A1 | 5/2016 | Kapur et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |

(56) References Cited

U.S. PATENT DOCUMENTS

| | | |
|---|---|---|
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0348691 A1 | 12/2017 | Bharadwaj et al. |
| 2017/0356027 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0087050 A1 | 3/2018 | Zheng et al. |
| 2018/0094298 A1 | 4/2018 | Hindson et al. |
| 2018/0094313 A1 | 4/2018 | Hindson |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0195112 A1 | 7/2018 | Lebofsky et al. |
| 2018/0216162 A1 | 8/2018 | Belhocine et al. |
| 2018/0236443 A1 | 8/2018 | Masquelier et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0327839 A1 | 11/2018 | Hindson et al. |
| 2018/0340939 A1 | 11/2018 | Gaublomme et al. |
| 2019/0134629 A1 | 5/2019 | Bernate et al. |
| 2019/0134633 A1 | 5/2019 | Bharadwaj et al. |

FOREIGN PATENT DOCUMENTS

| | | | |
|---|---|---|---|
| EP | 0249007 | A2 | 12/1987 |
| EP | 0271281 | A2 | 6/1988 |
| EP | 0637996 | B1 | 7/1997 |
| EP | 1019496 | B1 | 9/2004 |
| EP | 1672064 | A1 | 6/2006 |
| EP | 1482036 | B1 | 10/2007 |
| EP | 1841879 | A2 | 10/2007 |
| EP | 1594980 | B1 | 11/2009 |
| EP | 1967592 | B1 | 4/2010 |
| EP | 2258846 | A2 | 12/2010 |
| EP | 2145955 | B1 | 2/2012 |
| EP | 1905828 | B1 | 8/2012 |
| EP | 2136786 | B1 | 10/2012 |
| EP | 1908832 | B1 | 12/2012 |
| EP | 2540389 | A1 | 1/2013 |
| EP | 2635679 | A1 | 9/2013 |
| EP | 2752664 | A1 | 7/2014 |
| GB | 2097692 | B | 5/1985 |
| GB | 2485850 | A | 5/2012 |
| JP | S5949832 | A | 3/1984 |
| JP | S60227826 | A | 11/1985 |
| JP | 2006507921 | A | 3/2006 |
| JP | 2006289250 | A | 10/2006 |
| JP | 2007015990 | A | 1/2007 |
| JP | 2007268350 | A | 10/2007 |
| JP | 2009513948 | A | 4/2009 |
| JP | 2009208074 | A | 9/2009 |
| JP | 2012131798 | A | 7/2012 |
| WO | WO-8402000 | A1 | 5/1984 |
| WO | WO-9418218 | A1 | 8/1994 |
| WO | WO-9419101 | A1 | 9/1994 |
| WO | WO-9423699 | A1 | 10/1994 |
| WO | WO-9530782 | A1 | 11/1995 |
| WO | WO-9629629 | A2 | 9/1996 |
| WO | WO-9641011 | A1 | 12/1996 |
| WO | WO-9802237 | A1 | 1/1998 |
| WO | WO-9852691 | A1 | 11/1998 |
| WO | WO-9909217 | A1 | 2/1999 |
| WO | WO-9952708 | A1 | 10/1999 |
| WO | WO-0008212 | A1 | 2/2000 |
| WO | WO-0023181 | A1 | 4/2000 |
| WO | WO-0026412 | A1 | 5/2000 |
| WO | WO-0043766 | A1 | 7/2000 |
| WO | WO-0070095 | A2 | 11/2000 |
| WO | WO-0102850 | A1 | 1/2001 |
| WO | WO-0114589 | A2 | 3/2001 |
| WO | WO-0189787 | A2 | 11/2001 |
| WO | WO-0190418 | A1 | 11/2001 |
| WO | WO-0127610 | A3 | 3/2002 |
| WO | WO-0231203 | A2 | 4/2002 |
| WO | WO-02086148 | A1 | 10/2002 |
| WO | WO-0218949 | A3 | 1/2003 |
| WO | WO-03062462 | A2 | 7/2003 |
| WO | WO-2004002627 | A2 | 1/2004 |
| WO | WO-2004010106 | A2 | 1/2004 |
| WO | WO-2004061083 | A2 | 7/2004 |
| WO | WO-2004065617 | A2 | 8/2004 |
| WO | WO-2004069849 | A2 | 8/2004 |
| WO | WO-2004091763 | A2 | 10/2004 |
| WO | WO-2004102204 | A1 | 11/2004 |
| WO | WO-2004103565 | A2 | 12/2004 |
| WO | WO-2004105734 | A1 | 12/2004 |
| WO | WO-2005002730 | A1 | 1/2005 |
| WO | WO-2005021151 | A1 | 3/2005 |
| WO | WO-2005023331 | A2 | 3/2005 |
| WO | WO-2005040406 | A1 | 5/2005 |
| WO | WO-2005049787 | A2 | 6/2005 |
| WO | WO-2005082098 | A2 | 9/2005 |
| WO | WO-2006030993 | A1 | 3/2006 |
| WO | WO-2006078841 | A1 | 7/2006 |
| WO | WO-2006096571 | A2 | 9/2006 |
| WO | WO-2007001448 | A2 | 1/2007 |
| WO | WO-2007002490 | A2 | 1/2007 |
| WO | WO-2007012638 | A1 | 2/2007 |
| WO | WO-2007018601 | A1 | 2/2007 |
| WO | WO-2007024840 | A2 | 3/2007 |
| WO | WO-2007081385 | A2 | 7/2007 |
| WO | WO-2007081387 | A1 | 7/2007 |
| WO | WO-2007084192 | A2 | 7/2007 |
| WO | WO-2007089541 | A2 | 8/2007 |
| WO | WO-2007093819 | A2 | 8/2007 |
| WO | WO-2007111937 | A1 | 10/2007 |
| WO | WO-2007114794 | A1 | 10/2007 |
| WO | WO-2007121489 | A2 | 10/2007 |
| WO | WO-2007133710 | A2 | 11/2007 |
| WO | WO-2007138178 | A2 | 12/2007 |
| WO | WO-2007139766 | A2 | 12/2007 |
| WO | WO-2007140015 | A2 | 12/2007 |
| WO | WO-2007147079 | A2 | 12/2007 |
| WO | WO-2007149432 | A2 | 12/2007 |
| WO | WO-2008021123 | A1 | 2/2008 |
| WO | WO-2008091792 | A2 | 7/2008 |
| WO | WO-2008102057 | A1 | 8/2008 |
| WO | WO-2008109176 | A2 | 9/2008 |
| WO | WO-2008121342 | A2 | 10/2008 |
| WO | WO-2008061193 | A3 | 11/2008 |
| WO | WO-2008134153 | A1 | 11/2008 |
| WO | WO-2008150432 | A1 | 12/2008 |
| WO | WO-2009005680 | A1 | 1/2009 |
| WO | WO-2009011808 | A1 | 1/2009 |
| WO | WO-2009015296 | A1 | 1/2009 |
| WO | WO-2009048532 | A2 | 4/2009 |
| WO | WO-2009061372 | A1 | 5/2009 |
| WO | WO-2009085215 | A1 | 7/2009 |
| WO | WO-2009147386 | A1 | 12/2009 |
| WO | WO-2010004018 | A2 | 1/2010 |
| WO | WO-2010014604 | A1 | 2/2010 |

(56) References Cited

FOREIGN PATENT DOCUMENTS

| | | |
|---|---|---|
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011140627 A1 | 11/2011 |
| WO | WO-2012012037 A1 | 1/2012 |
| WO | WO-2012019765 A1 | 2/2012 |
| WO | WO-2012047889 A2 | 4/2012 |
| WO | WO-2012048340 A1 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014028537 A1 | 2/2014 |
| WO | WO-2014053854 A1 | 4/2014 |
| WO | WO-2014071361 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014150931 A1 | 9/2014 |
| WO | WO-2014182835 A1 | 11/2014 |
| WO | WO-2014189957 A2 | 11/2014 |
| WO | WO-2014210353 A2 | 12/2014 |
| WO | WO-2015031691 A1 | 3/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016170126 A1 | 10/2016 |
| WO | WO-2016176322 A1 | 11/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017053902 A1 | 3/2017 |
| WO | WO-2017053903 A1 | 3/2017 |
| WO | WO-2017053905 A1 | 3/2017 |
| WO | WO-2017075265 A1 | 5/2017 |
| WO | WO-2017156336 A1 | 9/2017 |
| WO | WO-2018045186 A1 | 3/2018 |
| WO | WO-2018119301 A1 | 6/2018 |
| WO | WO-2018191701 A1 | 10/2018 |
| WO | WO-2019028166 A1 | 2/2019 |

OTHER PUBLICATIONS

Abate, et al. Beating Poisson encapsulation statistics using close-packed ordering. Lab Chip. Sep. 21, 2009;9(18):2628-31. doi: 10.1039/b909386a. Epub Jul. 28, 2009.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Abate et al., Valve-based flow focusing for drop formation. Appl Phys Lett. 2009;94. 3 pages.

Abate et al., Syringe-vacuum microfluidics: A portable technique to create monodisperse emulsions, Biomicrofluidics 5, 014107 (2011).

Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.

Adamson et al., "Production of arrays of chemically distinct nanolitre plugs via repeated splitting in microfluidic devices", Lab Chip 6(9): 1178-1186 (Sep. 2006).

Adey, et al. Rapid, low-input, low-bias construction of shotgun fragment libraries by high-density in vitro transposition. Genome Biology 11:R119 (2010).

Adey, et al., "Ultra-low-input, tagmentation-based whole-genome bisulfite sequencing", Genome Research, 2012, 22 ;6): 1139-1143.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

Agresti, et al., "Ultra-high-throughput screening in drop-based microfluidics for directed evolution", vol. 107, No. 9 (Mar. 2, 2010).

Ahern, "Biochemical, Reagents Kits Offer Scientists Good Return on Investment" The Scientist (1995) 9(15):1-7.

Ahn et al., "Dielectrophoretic manipulation of drops for high-speed microfluidic sorting devices", Applied Physics Letter, 88 (2006).

"Ahn K, et al; Electrocoalescence of drops synchronized by size-dependent flow in microfluidic channels. Appl Phys Lett 88; (2006); pp. 264105-1-264105-3."

Aitman, et al. Copy numbert polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Bioi., 329: 196-205 (2006).

Akselband, "Rapid mycobacteria drug susceptibility testing using gel microdrop (GMD) growth assay and flow cytometry", J. Microbiol. Methods, 62:181-197 (2005).

Ali-Cherif et al., "Programmable Magnetic Tweezers and Droplet Microfluidic Device for High-Throughput Nanoliter Multi-Step Assays", Angew. Chem. Int. Ed. 51, 10765-10769 (2012).

Altemos et al., "Genomic Characterization of Large Heterochromatic Gaps in the Human Genome Assembly," PLOS Computational Biology, May 15, 2014, vol. 10, Issue 5, 14 pages.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna, S.L., et al., "Formation of dispersions using "flow focusing" in microchannels," Applied Physics Letters, vol. 82, No. 3, pp. 364-366 (2003).

Anonymous, "Oligo(dT)25 cellulose beads" NEB (2012) Retrieved from the Internet:https://www.neb.com/~/media/Catalog/All-Products/286CA51268E24DE1B06F1CB2886981354/Datacards%20or%Manuals/S1408Datasheet-Lot0011205.pdf.

Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.

Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.

(56) References Cited

OTHER PUBLICATIONS

Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Ason et al. DNA sequence bias during Tn5 transposition. Journal of molecular biology 335.5 (2004): 1213-1225.
Attia, et al. Micro-injection moulding of polymer microfluidic devices. Microfluidics and nanofluidics. 2009; 7(1):1-28.
Balikova, et al. Autosomal-dominant microtia linked to five tandem copy-number-variable region at chromosome 4p16. Am J Hum Genet. Jan. 2008;82(1):181-7. doi: 10.1016/j.ajhg.2007.08.001.
Bardin et al., "High-speed, clinical-scale microfluidic generation of stable phase-change droplets for gas embolotherapy", Lab Chip, Vo.11, 3990-3998 (2011).
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Baret et al., Kinetic aspects of emulsion stabilization by surfactants: a microfluidic analysis, Langmuir 25:6088-6093 (2009).
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Becker et al., "Polymer Microfabrication Technologies for Microfluidic", vol. 390, Issue 1, pp. 89-111 (Jan. 2008).
Belder "Microfluidics with Droplets", Angew. Chem. Int. Ed., 44, 3521-3522, (2005).
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bilotkach et al., "Fabrication of PDMS Membranes with Aqueous Molds for Microfluidic Systems", 12th Int'l Conference Miniaturized Sys. for Chemistry and Life Scis. (2008).
Bjornsson et al., Intra-individual change over time in DNA methylation with familial clustering, JAMA, Jun. 25, 2008, vol. 299 No. 24, pp. 2877-2883.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLoS One, vol. 7:1-10, 2012.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Brenner, et al. In vitro cloning of complex mixtures of DNA on microbeads: physical separation of differentially expressed cDNAs. Proc Natl Acad Sci U S A. Feb. 15, 2000;97(4):1665-70.
Brenner, et al., "Injection Molding of Microfluidic Chips by Epoxy-Based Master Tools" (Oct. 9, 2005).
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.

Brody, et al. Biotechnology at Low Reynolds Numbers. Biophys J. 1996; 71:3430-3441.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol.; 109: Jan. 29, 2021-Sep. 29, 2021. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio, et al. Nextera Technology for NGS DNA Library Preparation: Simultaneous Fragmentation and Tagging by in Vitro Transposition, Nextera Technology, 2009, 16-3, 1-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Chan et al., "High-Temperature Microfluidic Synthesis of CdSe Nanocrystals in Nanoliter Droplets", J. Am. Soc., 127, 13854-13861 (Oct. 12, 2005).
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.

(56) References Cited

OTHER PUBLICATIONS

Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Christopher et al., "Microfluidic methods for generating continuous droplet streams", J. Phys. D: Appl. Phys. 40, R319-R336 (2007).
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. 339.6121 (Feb. 15, 2013): 819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 16/033,065, filed Jul. 11, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/170,980, filed Oct. 25, 2018.
Co-pending UU.S. Appl. No. 16/180,356, filed Nov. 5, 2018.
Co-pending U.S. Appl. No. 16/180,378, filed Nov. 5, 2018.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dangla, et al. Droplet microfluidics driven by gradients of confinement. Proc Natl Acad Sci U S A. Jan. 15, 2013; 110(3): 853-858. Published online Jan. 2, 2013. doi: 10.1073/pnas.1209186110.
De Bruin et al., UBS Investment Research. Q-Series®: DNA Sequencing. UBS Securities LLC. Jul. 12, 2007. 15 pages.
Dekker, et al. Capturing chromosome conformation. Science. Feb. 15, 2002;295(5558):130611.
Demirci, et al. Single cell epitaxy by acoustic picolitre droplets. Lab Chip. Sep. 2007;7(9):1139- 45. Epub Jul. 10, 2007.
Dendukuri et al., "Controlled synthesis of nonspherical microparticles Using Microfluidics", Langmuir, 21, 2113-2116 (Feb. 11, 2005).
Depristo et al. A framework for variation discovery and genotyping using next-generation DNA sequencing data. Nature Genet 43:491-498 (2011).
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817- 8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Duffy, et al. Rapid Prototyping of Microfluidic Systems in Poly(dimethylsiloxane). Anal Chem. Dec. 1, 1998;70(23):4974-84. doi: 10.1021/ac980656z.
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Engl, et al., "Controlled production of emulsions and particles by milli- and microfluidic techniques", Current Opinion in Colloid and Interface Science, vol. 13, 206-216 (Sep. 26, 2007).
Epicentre., "EZ-Tn5TM Custom Transposome Construction Kits", http://www.epicentre.com, pp. 1-17, 2012.
Erbacher et al., "Towards Integrated Continuous-Flow Chemical Reactors", Mikrochimica Acta, 131, pp. 19-24 (1999).
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Ferraro et al., Microfluidic platform combining droplets and magnetic tweezers: application to HER2 expression in cancer diagnosis, Scientific Reports 6:25540 (May 9, 2016).
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology.1999; 17:1109-1111.
Fulton, et al. Advanced multiplexed analysis with the FlowMetrix system. Clin Chem. Sep. 1997;43(9):1749-56.

(56) References Cited

OTHER PUBLICATIONS

Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Garstecki, et al. Formation of monodisperse bubbles in a microfluidic flow-focusing device. Applied Physics Letters. 2004; 85(13):2649-2651. DOI: 10.1063/1.1796526.
Garstecki et al., "Mechanism for Flow-Rate Controlled Breakup in Confined Geometries: A Route to Monodisperse Emulsions", PRL 94, 164501 (Apr. 27, 2005).
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, X. et al. "CRISPR-Cas9 delivery to hard-to-transfect cells via membrane deformation" Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hettiarachchi et al., "Controllable microfluidic synthesis of multiphase drug-carrying liposheres for site-targeted therapy", American Inst. of Chem. Engineers (May 19, 2009).
Hiatt, et al. Parallel, tag-directed assembly of locally derived short sequence reads. Nat Methods. Feb. 2010;7(2):119-22. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
"How many species of bacteria are there" (wisegeek.com; accessed Jan. 21, 2014).
Hu et al., Shape Controllable Microgel Particles Prepared by Microfluidic Combining External Crosslinking, Biomicrofluidics 6:26502 (May 18, 2012).
"Huebner et al., "Microdroplets: A sea of applications?"; Lab on a Chip, 8; (2008); pp. 1244-1254, 2008".
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Hung, et al., "Alternating droplet generation and controlled dynamic droplet fusion in microfluidic device for Cds nanoparticle synthesis" (Jan. 5, 2006).
Hung et al., "PLGA micro/nanosphere synthesis by droplet microfluidic solvent evaporation and extraction approaches", Lab chip, vol. 10, 1820-1825 (May 14, 2010).
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to The University of Birmingham for the degree of Doctor of Philosophy. 2009.
Ivanova et al., "Droplet Formation in a Thin Layer of a Two-Component Solution under the Thermal Action of Laser Radiation", Colloid Journal, vol. 69, No. 6, pp. 735-740 (Feb. 19, 2007).
Jeffries et al., "Controlled Shrinkage and Re-expansion of a Single Aqueous Droplet inside an Optical Vortex Trap", , J. Phys. Chem. B, 2007, 111 (11), pp. 2806-2812.
Jeffries et al., "Dynamic modulation of chemical concentration in an aqueous droplet", Angew. Chem. Int. Ed., 1326-1328 (2007).
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Joanicot et al., "Droplet Control for Microfluidics", Science 309:887-888 (Aug. 2005).
Johnson, "Rapid microfluidic mixing", Analytical Chemistry, vol. 74, No. 1, pp. 45-51, (Jan. 1, 2002).
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Jung, et al. Micro machining of injection mold inserts for fluidic channel of polymeric biochips. Sensors. 2007; 7(8):1643-1654.

(56) References Cited

OTHER PUBLICATIONS

Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.

Katsura, et al. Indirect micromanipulation of single molecules in water-in-oil emulsion. Electrophoresis. Jan. 2001;22(2):289-93.

Kawari et al., Mass-Production System of Nearly Monodisperse Diameter Gel Particles Using Droplets Formation in a Microchannel, Micro Total Analysis Systems, vol. I, 368-370, Springer (2002).

Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.

Kenis, et al. Microfabrication Inside Capillaries Using Multiphase Laminar Flow Patterning. Science. 1999; 285:83-85.

Khomiakova et al., Analysis of perfect and mismatched DNA duplexes by a generic hexanucleotide microchip. Mol Biol(Mosk). Jul.-Aug. 2003;37(4):726-41. Russian. Abstract only.

Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.

Kim, et al. Fabrication of monodisperse gel shells and functional microgels in microfluidic devices. Angew Chem Int Ed Engl. 2007;46(11):1819-22.

Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.

Kirkness et al. "Sequencing of isolated sperm cells for direct haplotyping of a human genome," Genome Res (2013) 23:826-832.

"Kiss MM, et al. "High-Throughput Quantitative Polymerase Chain Reaction in Picoliter Droplets"; Anal Chem 80(23); (2008); pp. 8975-8981."

Kitzman et al. "Haplotype-resolved genome sequencing of a Gujarati Indian individual." Nat Biotechnol (2011) 29:59-63.

Kitzman, et al. Noninvasive whole-genome sequencing of a human fetus. Sci Transl Med. Jun. 6, 2012;4(137):137ra76. doi: 10.1126/scitranslmed.3004323.

Kivioja, et al. Counting absolute numbers of molecules using unique molecular identifiers. Nat Methods. Nov. 20, 2011;9(1):72-4.

Klein, et al. Droplet barcoding for single-cell transcriptomics applied to embryonic stem cells. Cell. May 21, 2015;161(5):1187-201. doi: 10.1016/j.cell.2015.04.044.

Knapp, et al. Generating barcoded libraries for multiplex high-throughput sequencing. Methods Mol Biol. 2012;840:155-70. doi: 10.1007/978-1-61779-516-9_19.

Knight, et al. Subtle chromosomal rearrangements in children with unexplained mental retardation. Lancet. Nov. 13, 1999;354(9191):1676-81.

Kobayashi, et al. Effect of slot aspect ratio on droplet formation from silicon straight-through microchannels. J Colloid Interface Sci. Nov. 1, 2004;279(1):277-80.

Kobayashi et al., "Straight-Through Microchannel Devices for Generating Monodisperse Emulsion Droplets Several Microns in Size", Microfluid Nanofluid 4:167-177, (Mar. 30, 2008).

Kohler et al., "Nanoliter Segment Formation in Micro Fluid Devices for Chemical and Biological Micro Serial Flow Processes in Dependence on Flow Rate and Viscosity", Sensors and Actuators A 119, 19-27 (Nov. 2, 2005).

Kolodeziejczyk et al., "The technology and biology of single-cell RNA sequencing", Molecular Cell, vol. 58 (May 21, 2015).

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip The Royal Soc. of Chem. 8: 1110-1115 (2008).

Kozarewa, et al, "96-plex molecular barcoding for the Illumina Genome Analyzer", Methods Mol Biol., 733:279-98, 2011.

Kozarewa, et al. "Amplification-free Illumina sequencing-library preparation facilitates improved mapping and assembly of GC-biased genomes", Nat Methods., 6: 291-5, 2009.

Kutyavin, et al. Oligonucleotides containing 2-aminoadenine and 2-thiothymine act as selectively binding complementary agents. Biochemistry. Aug. 27, 1996;35(34):11170-6.

Kwok, et al, "Single-molecule analysis for molecular haplotyping", Hum Mutat., 23:442-6, 2004.

Lagally, et al. Single-Molecular DNA Amplification and Analysis in an Integrated Microfluidic Device. Anal Chem. Feb. 1, 2001;73(3):565-70.

Lagus, et al. A review of the theory, methods and recent applications of high-throughput single-cell droplet microfluidics. J. Phys. D: Appl. Phys. (2013) 46:114005. (21 pages).

Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.

Laird et al, Hairpin-bisulfite PCR: Assessing epigenetic methylation patterns on complementary strands of individual DNA molecules, 2004, PNAS, 101, 204-209.

Lake, et al. "Integrative Single-Cell Analysis by Transcriptional and Epigenetic States in Human Adult Brain". Apr. 19, 2017. doi: https://doi.org/10.1101/128520.

Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].

Lander, et al. Initial sequencing and analysis of the human genome. Nature, 409 (Feb. 15, 2001): 860-921.

Lasken, et al. (1996) Archaebacterial DNA Polymerases Tightly Bind Uracil-containing DNA. The Journal of Biological Chemistry, 271(30):17692-17696 (Year: 1996).

Laulicht et al., Evaluation of continuous flow nanosphere formation by controlled microfluidic transport, American Chem. Society (Aug. 6, 2008).

Lebedev, A. et al. "Hot Start PCR with heat-activatable primers: a novel approach for improved PCR performance" NAR (2008) 36(20):E131-1.

Lee et al., "A tunable microflow focusing device utilizing controllable moving walls and its applications for formation of microdroplets in liquids", J. Micromech. Microeng. 17 1121-1129 (Jun. 2007).

Lee, et al. ACT-PRESTO: Rapid and consistent tissue clearing and labeling method for 3-dimensional (3D) imaging. Sci Rep. Jan. 11, 2016;6:18631. doi: 10.1038/srep18631.

Lee et al. Alginate: Properties and biomedical applications. Prog Polym Sci 37(1):106-126 (2012).

Lee et al., Double emulsion-templated nanoparticle colloidosomes with selective permeability. Adv Mater. 2008;20:3498-503. Month not cited on publication.

Lee, et al., "Highly multiplexed subcellular RNA sequencing in situ. Science. Mar. 21, 2014;343(6177):1360-3. doi: 10.1126/science.1250212. Epub Feb. 27, 2014."

Lee, et al., "Microfluidic air-liquid cavity acoustic transducers for on-chip integration of sample preparation and sample detection" (Dec. 2010).

Lee, J-H. et al. "Fluorescent in situ sequencing (FISSEQ) of RNA for gene expression profiling in intact cells and tissues" Nature Protocols (Feb. 12, 2015) 10(3):442-458.

"Lennon et al. A scalable, fully automated process for construction of sequence-ready barcoded libraries for 454. Genome Biology 11:R15 (2010)."

(56) References Cited

OTHER PUBLICATIONS

Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, et al. Step-emulsification in a microfluidic device. Lab Chip. Feb. 21, 2015;15(4):1023-31. doi: 10.1039/c4lc01289e.
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
"List of sequenced bacterial genomes" (Wikipedia.com; accessed Jan. 24, 2014).
Liu et. al., "Droplet formation in a T-shaped microfluidic junction", Journal of Applied Physics vol. 106, 034906 (Aug. 7, 2009).
Liu et al., "Droplet-based synthetic method using microflow focusing and droplet fusion", Microfluid Nanofluid, vol. 3, 239-24 (2007).
Liu et al., Dynamics of coalescence of plugs with a hydrophilic wetting layer induced by flow in a microfluidic chemistrode (Dec. 9, 2008).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Lorenceau, E., et al., "Generation of Polymerosomes from Double-Emulsions," Langmuir, vol. 21, pp. 9183-9186 (2005).
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):543- 7.
Maan, et al. Spontaneous droplet formation techniques for monodisperse emulsions preparation—Perspectives for food applications. Journal of Food Engineering. vol. 107, Issues 3-4, Dec. 2011, pp. 334-346.
Macaulay; et al., "G&T-seq: parallel sequencing of single-cell genomes and transcriptomes. Nature Methods, 2015, p. 1-7."
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Malic et al., "Integration and detection of biochemical assays in digital microfluidic LOC devices", Lab Chip, vol. 10, 418-431 (2010).
Malsch et al., "µPIV-Analysis of Taylor flow in micro channels", Chemical Engineering Journal, 135S, S166-S172 (2008).

Man. Monolithic Structures for Integrated Microfluidic Analysis. PhD Thesis. 2001.
Marcus. Gene method offers diagnostic hope. The Wall Street Journal. Jul. 11, 2012.
Maricic T, et al. Optimization of 454 sequencing library preparation from small amounts of DNA permits sequence determination of both DNA strands. Biotechniques. Jan. 2009; 46(1):51-2, 54-7.
"Mary P Pascaline, et al; "Controlling droplet incubation using close-packed plug flow"; Biomicrofluidics 5; (2011); pp. 024101-1-024101-6."
Mason, T.J. and Bibette, J. Shear Rupturing of Droplets in Complex Fluids, Langmuir, 13(17):4600-4613 (1997).
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis et al., Droplet-Based Microfluidic Systems for High-Throughput Single DNA Molecule Isothermal Amplification and Analysis, Anal Chem 81(12):4813-4821 (2009).
Mazutis, et al., Preparation of monodisperse emulsions by hydrodynamic size fractionation (Nov. 18, 2009).
Mazutis, et al. Selective droplet coalescence using microfluidic systems. Lab Chip. Apr. 24, 2012;12(10):1800-6. doi: 10.1039/c2lc40121e. Epub Mar. 27, 2012.
McGinnis, et al. Multi-seq: Scalable sample multiplexing for single-cell RNA sequencing using lipid-tagged indices. bioRxiv 387241; doi: https://doi.org/10.1101/387241.
Meier et al., "Plug-Based Microfluidics with Defined Surface Chemistry to Miniaturize and control aggregation of amyloidogenic peptides", Angew Chem. Ed Engl., 48(8), 1487-1489 (2009).
Merriman, et al. Progress in ion torrent semiconductor chip based sequencing. Electrophoresis. Dec. 2012;33(23):3397-417. doi: 10.1002/elps.201200424.
Microfluidic ChipShop, Microfluidic Product Catalogue (Feb. 2005).
Microfluidic ChipShop. Microfluidic product catalogue. Mar. 2005.
Microfluidic ChipShop. Microfluidic product catalogue. Oct. 2009.
Miller JC, et al. An improved zinc-finger nuclease architecture for highly specific genome editing. Nat. Biotechnol. 2007;25:778-785.
Miller-Stephenson Chemicals 157 FS Series catalog, www.miller-stephenon.com.
miRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-ddimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_nin_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.

(56) References Cited

OTHER PUBLICATIONS

Narayanan, J. et al. "Determination of agarose gel pore size: Absorbance measurements vis a vis other techniques" Journal of Physics: Conference Series 28 (2006) 83-86 (Year: 2006).
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako et al., "Novel microreactors for functional polymer beads", Chemical Engineering Journal 101 23-29 (Nov. 19, 2004).
Nisisako et al., "Synthesis of Monodisperse Bicolored Janus Particles with Electrical Aniaotropy Using a Microfluidic Co-Flow System", Adv. Mater., 18, 1152-1156.
Nisisako, T. et al. "Droplet Formation in a Microchannel on PMMA Plate" Abstract. 2001 Kluwer Academic Publishers. p. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Niu et al., A hybrid microfluidic chip for digital electro-coalescence of droplets, (Nov. 2009).
Niu et al. "Droplet-based compartmentalization of chemically separated components in two-dimensional separations", Chem. Commun, 6159-6161 (Sep. 15, 2009).
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677- 82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production ofMonodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Ong et al., Experimental and computational analysis of droplet formation in a high-performance flow-focusing geometry, Sensors and Actuators A 138, 203-212 (May 4, 2007).
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics.,13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Perroud et al., "Isotropically etched radial micropore for cell concentration, immobilization, and picodroplet generation", Lab Chip, 9, 507-515 (Jan. 7, 2009).
Peters, B.A. et al. Accurate whole-genome sequencing and haplotyping from 10 to 20 human cells. Nature, 487(7406):190-195 (Jul. 11, 2012).

Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013).
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.

(56) References Cited

OTHER PUBLICATIONS

Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sahin, et al. Microfluidic EDGE emulsification: the importance of interface interactions on droplet formation and pressure stability. Sci Rep. May 27, 2016;6:26407. doi: 10.1038/srep26407.
Sakaguchi, et al. (1996) Cautionary Note on the Use of dUMP-Containing PCR Primers with Pfu and VentR. Biotechniques, 21(3): 369-370 (Year: 1996).
Sander JD, et al. Selection-free zinc-finger-nuclease engineering by context-dependent assembly (CoDA). Nat. Methods. 2011;8:67-69.
Savva, et al. The structural basis of specific base-excision repair by uracil-DNA glycosylase. Nature. Feb. 9, 1995;373(6514):487-93.
Schirinzi et al., Combinatorial sequencing-by-hybridization: Analysis of the NF1 gene. Genet Test. Spring 2006;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Sessoms et al., "Droplet motion in microfluidic networks: Hydrodynamic interactions and pressure-drop measurements", Physical Review, E 80, 016317 (Jul. 31, 2009).
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shaikh, et al. A modular microfluidic architecture for integrated biochemical analysis. Proc Natl Acad Sci U S A. Jul. 12, 2005;102(28):9745-50. Epub Jun. 28, 2005.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/g m62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Simon, et al., "Using formaldehyde-assisted isolation of regulatory elements (FAIRE) to isolate active regulatory DNA", Nature Protocols, 2012, 7(2): 256-267.
Skerra. Phosphorothioate primers improve the amplification of DNA sequences by DNA polymerases with proofreading activity. Nucleic Acids Res. Jul. 25, 1992; 20(14):3551-4.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Spormann Laboratory, Polymerase Chain Reaction (PCR), Alfred Spormann Laboratory, 2009, 1-3. (Year: 2009).
Srisa-Art et al., "High-throughput DNA droplet assays using Picoliter reactor volumes", Anal. Chem. vol. 79, 6682-6689 (Sep. 9, 2007).
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998).
Tayyab, S. et al. "Size exclusion chromatography and size exclusion HPLC of proteins" Biochem Ed, Pergamon, (1991) 19(3):149-152.
Tetradis-Meris et al., Novel parallel integration of microfluidic device network for emulsion formation. Ind. Eng. Chem. Res., 2009; 48 (19): 8881-8889.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.

(56) References Cited

OTHER PUBLICATIONS

ThermoFisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1) 107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Umbanhowar, P.B., et al., "Monodisperse Emulsion Generation via Drop Break Off in a Coflowing Stream," Langmuir, vol. 16, pp. 347-351 (2000).
Ushijima et al, Detection and interpretation of altered methylation patterns in cancer cells, 2005, Nature reviews, 5, 223-231.
Van Dijke, et al. Effect of viscosities of dispersed and continuous phases in microchannel oil-in-water emulsification . Microfluid Nanofluid (2010) 9: 77. https://doi.org/10.1007/s10404-009- 0521-7.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone. 0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Reverse transcriptase template switching: a SMART approach for full-length cDNA library construction. Biotechniques. Apr. 2001;30(4):892-7.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Hum• Antibodies Hybridomas. Jan. 1992;3 (1 ):14-8.

(56) References Cited

OTHER PUBLICATIONS

Zong et al. Genome-Wide Detection of Single Nucleotide and Copy Number Variations of a Single Human Cell. Science 338(6114):1622-1626 (2012).
Co-pending U.S. Appl. No. 16/419,820, filed May 22, 2019.

* cited by examiner

INSTRUMENT SYSTEMS FOR INTEGRATED SAMPLE PROCESSING

STATEMENT REGARDING FEDERALLY SPONSORED RESEARCH

Not Applicable

BACKGROUND OF THE INVENTION

The field of life sciences has experienced dramatic advancement over the last two decades. From the broad commercialization of products that derive from recombinant DNA technology, to the simplification of research, development and diagnostics, enabled by the invention and deployment of critical research tools, such as the polymerase chain reaction, nucleic acid array technologies, robust nucleic acid sequencing technologies, and more recently, the development and commercialization of high throughput next generation sequencing technologies. All of these improvements have combined to advance the fields of biological research, medicine, diagnostics, agricultural biotechnology, and myriad other related fields by leaps and bounds.

Many of these advances in biological analysis and manipulation require complex, multi-step process workflows, as well as multiple highly diverse unit operations, in order to achieve the desired result. Nucleic acid sequencing, for example requires multiple diverse steps in the process workflow (e.g., extraction, purification, amplification, library preparation, etc.) before any sequencing operations are performed. Each workflow process step and unit operation introduces the opportunity for user intervention and its resulting variability, as well as providing opportunities for contamination, adulteration, and other environmental events that can impact the obtaining of accurate data, e.g., sequence information.

The present disclosure describes systems and processes for integrating multiple process workflow steps in a unified system architecture that also integrates simplified sample processing steps.

BRIEF SUMMARY OF THE INVENTION

Provided are integrated systems and processes for use in the preparation of samples for analysis, and particularly for the preparation of nucleic acid containing samples for sequencing analysis.

According to various embodiments of the present invention, an integrated system for processing and preparing samples for analysis comprises a microfluidic device including a plurality of parallel channel networks for partitioning the samples including various fluids, and connected to a plurality of inlet and outlet reservoirs, at least a portion of the fluids comprising reagents, a holder including a closeable lid hingedly coupled thereto, in which in a closed configuration, the lid secures the microfluidic device in the holder, and in an open configuration, the lid comprises a stand orienting the microfluidic device at a desired angle to facilitate recovery of partitions or droplets from the partitioned samples generated within the microfluidic device. The integrated system may further include an instrument configured to receive the holder and apply a pressure differential between the plurality of inlet and outlet reservoirs to drive fluid movement within the channel networks.

In some embodiments, the desired angle at which the microfluidic device is oriented by the lid ranges from 20-70 degrees, 30-60 degrees, 40-50 degrees.

In some embodiments, the desired angle at which the microfluidic device is oriented by the lid is 45 degrees.

In some embodiments, the instrument comprises a retractable tray supporting and seating the holder, and slidable into out of the instrument, a depressible manifold assembly configured to be actuated and lowered to the microfluidic device and to sealaby interface with the plurality of inlet and outlet reservoirs, at least one fluid drive component configured to apply the pressure differential between the plurality of inlet and outlet reservoirs, and a controller configured to operate the at least one drive fluid component to apply the pressure differential depending on a mode of operation or according to preprogrammed instructions.

In some embodiments, at least one of the parallel channel networks comprises a plurality of interconnected fluid channels fluidly communicated at a first channel junction, at which an aqueous phase containing at least one of the reagents is combined with a stream of a non-aqueous fluid to partition the aqueous phase into discrete droplets within the non-aqueous fluid, and the partitioned samples are stored in the outlet reservoirs for harvesting, or stored in at least one product storage vessel.

In some embodiments, the plurality of interconnected fluid channels comprises a microfluidic structure having intersecting fluid channels fabricated into a monolithic component part.

In some embodiments, the integrated system further comprises a gasket coupled to the holder and including a plurality of apertures, in which when the lid is in the closed configuration, the gasket is positioned between the reservoirs and the manifold assembly to provide the sealable interface, and the apertures allow pressure communication between at least one of the outlet and the inlet reservoirs and the at least one fluid drive component.

In some embodiments, the integrated system further comprises springs to bias the manifold assembly in a raised position, and a servo motor to actuate and lower the manifold assembly.

In some embodiments, the integrated system further comprises at least one monitoring component interfaced with at least one of the plurality of channel networks and configured to observe and monitor characteristics and properties of the at least one channel network and fluids flowing therein. The at least one monitoring component is selected from the group consisting of: a temperature sensor, a pressure sensor, and a humidity sensor.

In some embodiments, the integrated system further comprises at least one valve to control flow into a segment of at least one channel of the plurality of parallel channel networks by breaking capillary forces acting to draw aqueous fluids into the channel at a point of widening of the channel segment in the valve.

In some embodiments, the at least one valve comprises a passive check valve.

In some embodiments, at least one of the plurality of parallel channel networks comprises a first channel segment fluidly coupled to a source of barcode reagents, a second channel segment fluidly coupled to a source of the samples, the first and second channel segments fluidly connected at a first channel junction, a third channel segment connected to the first and second channel segments at the first channel junction, a fourth channel segment connected to the third channel segment at a second channel junction and connected to a source of partitioning fluid, and a fifth channel segment fluidly coupled to the second channel junction and connected to a channel outlet, The at least one fluid driving system is coupled to at least one of the first, second, third, fourth, and fifth channel segments, and is configured to drive flow of the barcode reagents and the reagents of the sample into the first channel junction to form a reagent mixture in the third channel segment and to drive flow of the reagent mixture and the partitioning fluid into the second channel junction to form droplets of the first reaction mixture in a stream of partitioning fluid within the fifth channel segment.

According to various embodiments of the present invention, a holder assembly comprises a holder body configured to receive a microfluidic device, the microfluidic device including a plurality of parallel channel networks for partitioning various fluids, and a closeable lid hingedly coupled to the holder body. In a closed configuration, the lid secures the microfluidic device in the holder body, and in an open configuration, the lid comprises a stand to orient the microfluidic device at a desired angle to facilitate recovery of partitions or droplets from the partitioned fluids without spilling the fluids.

In some embodiments, the desired angle at which the microfluidic device is oriented by the lid ranges from 20-70 degrees, 30-60 degrees, 40-50 degrees.

In some embodiments, the desired angle at which the microfluidic device is oriented by the lid is 45 degrees.

According to various embodiments of the present invention, a method for measurement of parameters of fluid in samples for analysis in a microfluidic device of an integrated system comprises positioning a line camera in optical communication with a segment of at least one fluid channel of the microfluidic device, imaging, by the at least one line scan camera, in a detection line across the channel segment, and processing, by the at least one line scan camera, images of particulate or droplet based materials of the samples as the materials pass through the detection line, to determine shape, size and corresponding characteristics of the materials, and angling the at least one line camera and the corresponding detection line across the channel segment to increase a resolution of resulting images across the channel segment. An angle at which the at least one line camera and the corresponding detection line are angled across the channel segment ranges from 5-80 degrees from an axis perpendicular to the channel segment.

In some embodiments, the method for measurement further comprises optically communicating the line camera with a post partitioning segment of at least one fluid channel of the microfluidic device, to monitor formed partitions emanating from a partitioning junction of the microfluidic device.

In some embodiments, the method for measurement further comprises optically communicating the line camera with a post partitioning segment of at least one fluid channel of the microfluidic device, to monitor formed partitions emanating from a partitioning junction of the microfluidic device.

In some embodiments, the method for measurement further comprises optically coupling at least one line scan sensor to one or more of a particle inlet channel segment to monitor materials being brought into a partitioning junction to be co-partitioned.

DETAILED DESCRIPTION OF THE INVENTION

The present invention is directed to devices and systems for use in apportioning reagents and other materials into extremely large numbers of partitions in a controllable manner. In particularly preferred aspects, these devices and systems are useful in apportioning multiple different reagents and other materials, including for example, beads, particles and/or microcapsules into large numbers of partitions along with other reagents and materials. In particularly preferred aspects, the devices and systems apportion reagents and other materials into droplets in an emulsion in which reactions may be carried out in relative isolation from the reagents and materials included within different partitions or droplets. Also included are systems that include the above devices and systems for conducting a variety of integrated reactions and analyses using the apportioned reagents and other materials. Thus, the systems and processes of the present invention can be used with any devices and any systems such as those outlined in U.S. Provisional Patent Application No. 62/075,653, the full disclosure of which is expressly incorporated by reference in its entirety for all purposes, specifically including the Figures, Legends and descriptions of the Figures and components therein.

I. Partitioning Systems

The systems described herein include instrumentation, components, and reagents for use in partitioning materials and reagents. In preferred aspects, the systems are used in the delivery of highly complex reagent sets to discrete partitions for use in any of a variety of different analytical and preparative operations. The systems described herein also optionally include both upstream and downstream subsystems that may be integrated with such instrument systems.

Figure 1:
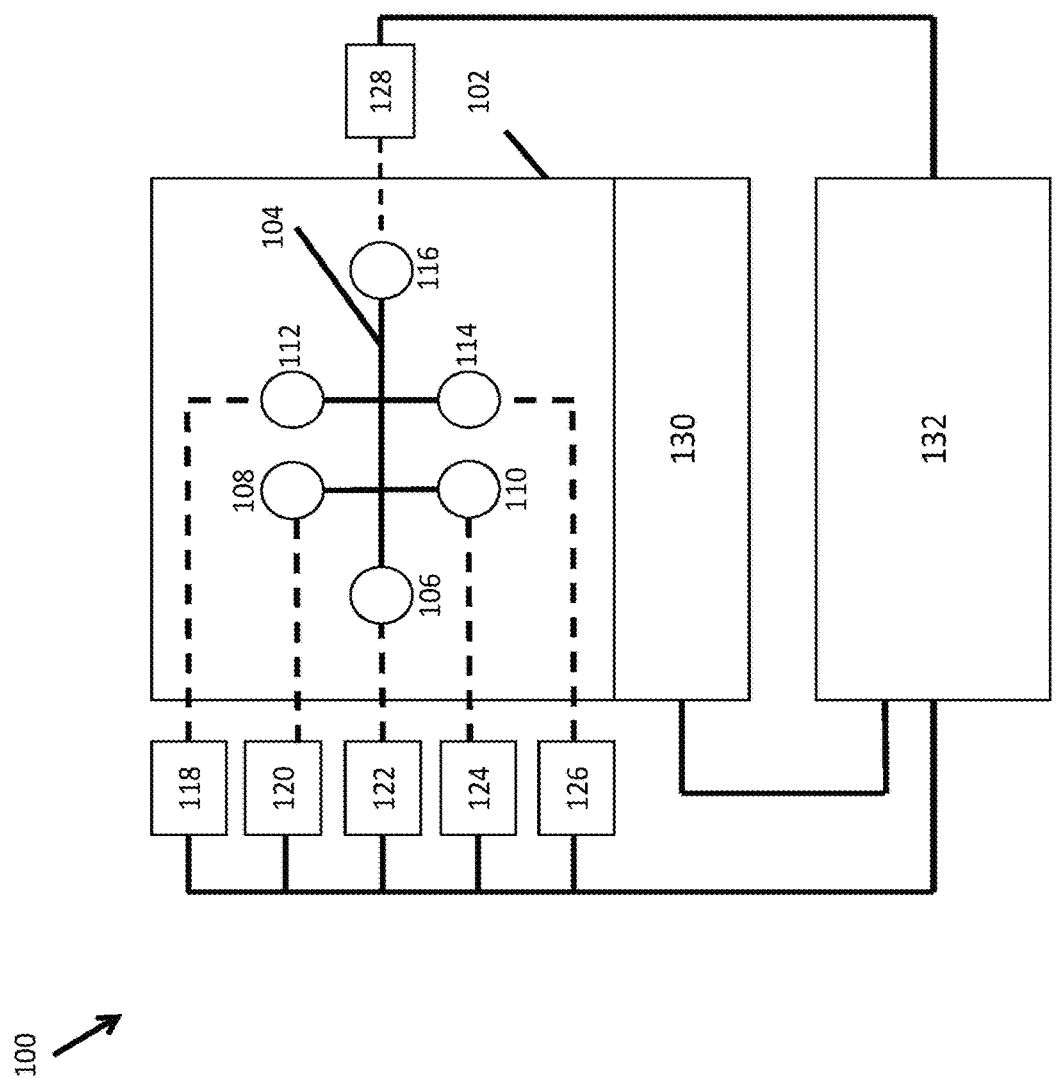
FIG. 1 schematically illustrates a first level of system architecture as further described herein.

The overall architecture of these systems typically includes a partitioning component, which is schematically illustrated in FIG. 1. As shown, the architecture 100, includes a fluidics component 102 (illustrated as an interconnected fluid conduit network 104), that is interfaced with one or more reagent and/or product fluid storage vessels, e.g., vessels 106-116. The fluidics component includes a network of interconnected fluid conduits through which the various fluids are moved from their storage vessels, and brought together in order to apportion the reagents and other materials into different partitions, which partitions are then directed to the product storage vessel(s), e.g., vessel 116.

The fluidics component 102 is typically interfaced with one or more fluid drive components, such as pumps 118-126, and/or optional pump 128, which apply a fluid driving force to the fluids within the vessels to drive fluid flow through the fluidic component. By way of example, these fluid drive components may apply one or both of a positive and/or negative pressure to the fluidic component, or to the vessels connected thereto, to drive fluid flows through the fluid conduits. Further, although shown as multiple independent pressure sources, the pressure sources may comprise a single pressure source that applies pressure through a manifold to one or more of the various channel termini, or a negative pressure to a single outlet channel terminus, e.g., pump 128 at reservoir 116.

The instrument system 100 also optionally includes one or more environmental control interfaces, e.g., environmental control interface 130 operably coupled to the fluidic component, e.g., for maintaining the fluidic component at a desired temperature, desired humidity, desired pressure, or otherwise imparting environmental control. A number of additional components may optionally be interfaced with the fluidics component and/or one or more of the reagent or product storage vessels 106-116, including, e.g., optical detection systems for monitoring the movement of the fluids and/or partitions through the fluidic component, and/or in the reagent and or product reservoirs, etc., additional liquid handling components for delivering reagents and/or products to or from their respective storage vessels to or from integrated subsystems, and the like.

The instrument system also may include integrated control software or firmware for instructing the operation of the various components of the system, typically programmed into a connected processor 132, which may be integrated into the instrument itself, or maintained on a directly or wirelessly connected, but separate processor, e.g., a computer, tablet, smartphone, or the like, for controlling the operation of, and/or for obtaining data from the various subsystems and/or components of the overall system.

II. Fluidics Component

As noted above, the fluidics component of the systems described herein is typically configured to allocate reagents to different partitions, and particularly to create those partitions as droplets in an emulsion, e.g., an aqueous droplet in oil emulsion. In accordance with this objective, the fluidic component typically includes a plurality of channel or conduit segments that communicate at a first channel junction at which an aqueous phase containing one or more of the reagents is combined with a stream of a non-aqueous fluid, such as an oil like a fluorinated oil, for partitioning the aqueous phase into discrete droplets within the flowing oil stream. While any of a variety of fluidic configurations may be used to provide this channel junction, including, e.g., connected fluid tubing, channels, conduits or the like, in particularly preferred aspects, the fluidic component comprises a microfluidic structure that has intersecting fluid channels fabricated into a monolithic component part. Examples of such microfluidic structures have been generally described in the art for a variety of different uses, including, e.g., nucleic acid and protein separations and analysis, cell counting and/or sorting applications, high throughput assays for, e.g., pharmaceutical candidate screening, and the like.

Typically, the microfluidics component of the system includes a set of intersecting fluid conduits or channels that have one or more cross sectional dimensions of less than about 200 um, preferably less than about 100 um, with some cross sectional dimensions being less than about 50 um, less than about 40 um, less than about 30 um, less than about 20 um, less than about 10 um, and in some cases less than or equal to about 5 um. Examples of microfluidic structures that are particularly useful in generating partitions are described herein and in U.S. Provisional Patent Application No. 61/977,804, filed Apr. 4, 2014, the full disclosure of which is incorporated herein by reference in its entirety for all purposes.

Figure 2:
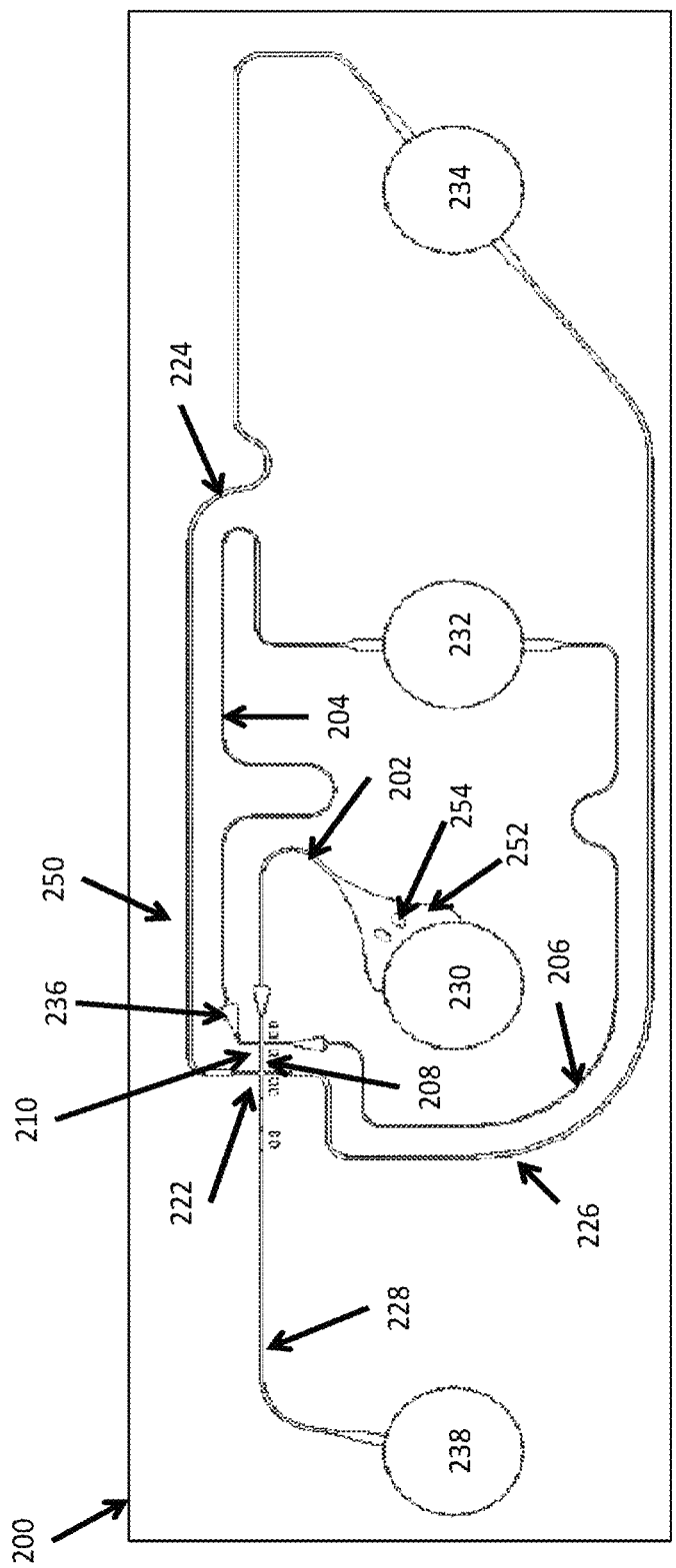
FIG. 2 is an exemplary illustration of a consumable microfluidic component for use in partitioning sample and other materials.

FIG. 2 shows an exemplary microfluidic channel structure for use in generating partitioned reagents, and particularly for use in co-partitioning two or more different reagents or materials into individual partitions. As shown, the microfluidic component 200 provides one or more channel network modules 250 for generating partitioned reagent compositions. As shown, the channel network module 250 includes a basic architecture that includes a first channel junction 210 linking channel segments 202, 204 and 206, as well as channel segment 208 that links first junction 210 to second channel junction 222. Also linked to second junction 222 are channel segments 224, 226 and 228.

As illustrated, channel segment 202 is also fluidly coupled to reservoir 230, that provides, for example, a source of additional reagents such as microcapsules, beads, particles or the like, optionally including one or more encapsulated or associated reagents, suspended in an aqueous solution. Each of channel segments 204 and 206 are similarly fluidly coupled to reagent storage vessel or fluid reservoir 232, which may provide for example, a source of sample material as well as other reagents to be partitioned along with the microcapsules. As noted previously, although illustrated as both channel segments 204 and 206 being coupled to the same reservoir 232, these channel segments are optionally coupled to different reservoirs for introducing different reagents or materials to be partitioned along with the reagents from reservoir 230.

As shown, each of channel segments 202, 204 and 206 are provided with optional additional fluid control structures, such as passive fluid valve 236. These valves optionally provide for controlled filling of the overall devices by breaking the capillary forces that draw the aqueous fluids into the device at the point of widening of the channel segment in the valve structure. Briefly, aqueous fluids are introduced first into the device in reservoirs 230 and 232, at which point these fluids will be drawn by capillary action into their respective channel segments. Upon reaching the valve structure, the widened channel will break the capillary forces, and fluid flow will stop until acted upon by outside forces, e.g., positive or negative pressures, driving the fluid into and through the valve structure. These structures are also particularly useful as flow regulators for instances where beads, microcapsules or the like are included within the reagent streams, e.g., to ensure a regularized flow of such particles into the various channel junctions.

Also shown in channel segment 202 is a funneling structure 252, that provides reduced system failure due to channel clogging, and also provides an efficient gathering structure for materials from reservoir 230, e.g., particles, beads or microcapsules, and regulation of their flow. As also shown, in some cases, the connection of channel segment 202 with reservoir 230, as well as the junctions of one or more or all of the channel segments and their respective reservoirs, may be provided with additional functional elements, such as filtering structures 254, e.g., pillars, posts, tortuous fluid paths, or other obstructive structures to prevent unwanted particulate matter from entering or proceeding through the channel segments.

First junction 210 is fluidly coupled to second junction 222. Also coupled to channel junction 222 are channel segments 224 and 226 that are, in turn fluidly coupled to reservoir 234, which may provide, for example, partitioning fluid that is immiscible with the aqueous fluids flowing from junction 210. Again, channel segments 224 and 226 are illustrated as being coupled to the same reservoir 234, although they may be optionally coupled to different reservoirs, e.g., where each channel segment is desired to deliver a different composition to junction 222, e.g., partitioning fluids having different make up, including differing reagents, or the like.

In exemplary operation, a first fluid reagent, e.g., including microcapsules or other reagents, that is provided in reservoir 230 is flowed through channel segment 202 into first channel junction 210. Within junction 210, the aqueous first fluid reagent solution is contacted with the aqueous fluids, e.g., a second reagent fluid, from reservoir 232, as introduced by channel segments 204 and 206. While illustrated as two channel segments 204 and 206, it will be appreciated that fewer (1) or more channel segments may be connected at junction 210. For example, in some cases, junction 210 may comprise a T junction at which a single side channel meets with channel segment 202 in junction 210.

The combined aqueous fluid stream is then flowed through channel segment 208 into second junction 222. Within channel junction 222, the aqueous fluid stream flowing through channel segment 208, is formed into droplets within the immiscible partitioning fluid introduced from channel segments 224 and 226. In some cases, one or both of the partitioning junctions, e.g., junction 222 and one or more of the channel segments coupled to that junction, e.g., channel segments 208, 224, 226 and 228, may be further configured to optimize the partitioning process at the junction.

Further, although illustrated as a cross channel intersection at which aqueous fluids are flowed through channel segment 208 into the partitioning junction 222 to be partitioned by the immiscible fluids from channel segments 224 and 226, and flowed into channel segment 228, as described elsewhere herein, partitioning structure within a microfluidic device of the invention may comprise a number of different structures.

As described in greater detail below, the flow of the combined first and second reagent fluids into junction 222, and optionally, the rate of flow of the other aqueous fluids and/or partitioning fluid through each of junctions 210 and 222, are controlled to provide for a desired level of partitioning, e.g., to control the number of frequency and size of the droplets formed, as well as control apportionment of other materials, e.g., microcapsules, beads or the like, in the droplets.

Once the reagents are allocated into separate partitions, they are flowed through channel segment 228 and into a recovery structure or zone, where they may be readily harvested. As shown, the recovery zone includes, e.g., product storage vessel or outlet reservoir 238. Alternatively, the recovery zone may include any of a number of different interfaces, including fluidic interfaces with tubes, wells, additional fluidic networks, or the like. In some cases, where the recovery zone comprises an outlet reservoir, the outlet reservoir will be structured to have a volume that is greater than the expected volume of fluids flowing into that reservoir. In its simplest sense, the outlet reservoir may, in some cases, have a volume capacity that is equal to or greater than the combined volume of the input reservoirs for the system, e.g., reservoirs 230, 232 and 234.

In certain aspects, and as alluded to above, at least one of the aqueous reagents to be co-partitioned will include a microcapsule, bead or other microparticle component, referred to herein as a bead. As such, one or more channel segments may be fluidly coupled to a source of such beads. Typically, such beads will include as a part of their composition one or more additional reagents that are associated with the bead, and as a result, are co-partitioned along with the other reagents. In many cases, the reagents associated with the beads are releasably associated with, e.g., capable of being released from, the beads, such that they may be released into the partition to more freely interact with other reagents within the various partitions. Such release may be driven by the controlled application of a particular stimulus, e.g., application of a thermal, chemical or mechanical stimulus. By providing reagents associated with the beads, one may better control the amount of such reagents, the composition of such reagents being co-partitioned, and the initiation of reactions through the controlled release of such reagents.

By way of example, in some cases, the beads may be provided with oligonucleotides releasably associated with the beads, where the oligonucleotides represent members of a diverse nucleic acid barcode library, whereby an individual bead may include a large number of oligonucleotides, but only a single type of barcode sequence included among those oligonucleotides. The barcode sequences are co-partitioned with sample material components, e.g., nucleic acids, and used to barcode portions of those sample components. The barcoding then allows subsequent processing of the sequence data obtained, by matching barcodes as having derived from possibly structurally related sequence portions. The use of such barcode beads is described in detail in U.S. patent application Ser. No. 14/316,318, filed Jun. 26, 2014, and incorporated herein by reference in its entirety for all purposes.

The microfluidic component is preferably provided as a replaceable consumable component that can be readily replaced within the instrument system, e.g., as shown in FIG. 2. For example, microfluidic devices or chips may be provided that include the integrated channel networks described herein, and optionally include at least a portion of the applicable reservoirs, or an interface for an attachable reservoir, reagent source or recovery component as applicable. Fabrication and use of microfluidic devices has been described for a wide range of applications, as noted above. Such devices may generally be fabricated from organic materials, inorganic materials, or both. For example, microfluidic devices may be fabricated from organic materials, such as polyethylene or polyethylene derivatives, such as cyclic olefin copolymers (COC), polymethylmethacrylate (PMMA), polydimethylsiloxane (PDMS), polycarbonate, polystyrene, polypropylene, or the like, or they may be fabricated in whole or in part from inorganic materials, such as silicon, or other silica based materials, e.g., glass, quartz, fused silica, borosilicate glass, or the like. Particularly useful microfluidic device structures and materials are described in Provisional U.S. Patent Application No. 61/977,804, filed Apr. 4, 2014, previously incorporated herein by reference.

III. Flow Controllers

As noted with reference to FIG. 1, above, typically, such replaceable microfluidics structures are integrated within a larger instrument system that, as noted above, includes a number of other components for operation of the system, as well as optional additional system components used for monitoring system operation, and/or for processes in a workflow that sit upstream and/or downstream of the partitioning processes.

In particular, as noted above, the overall system typically includes one or more fluid driving systems for driving flow of the fluid reagents through the channel structures within the fluidic component(s). Fluid driving systems can include any of a variety of different fluid driving mechanisms. In preferred aspects, these fluid driving systems will include one or more pressure sources interfaced with the channel structures to apply a driving pressure to either push or pull fluids through the channel networks. In particularly preferred aspects, these pressure sources include one or more pumps that are interfaced with one or more of the inlets or outlets to the various channel segments in the channel network.

As will be appreciated, in some cases, fluids are driven through the channel network through the application of positive pressures by applying pressures to each of the inlet reservoirs through the interconnected channel segments. In such cases, one or more pressure sources may be interfaced with each reservoir through an appropriate manifold or connector structure. Alternatively, a separately controllable pressure source may be applied to each of one or more of the various different inlet reservoirs, in order to independently control the application of pressure to different reservoirs. Such independent control can be useful where it is desired to adjust or modify of flow profiles in different channel segments over time or from one application to another. Pressure pumps, whether for application of positive or negative pressure or both, may include any of a variety of pumps for application of pressure heads to fluid materials, including, for example, diaphragm pumps, simple syringe pumps, or other positive displacement pumps, pressure tanks or cartridges along with pressure regulator mechanisms, e.g., that are charged with a standing pressure, or the like.

As noted, in certain cases, a negative pressure source may be applied to the outlet of the channel network, e.g., by interfacing the negative pressure source with outlet reservoir 238 shown in FIG. 2. By applying a negative pressure to the outlet, the ratios of fluid flow within all of the interconnected channels is generally maintained as relatively constant, e.g., flow within individual channels are not separately regulated through the applied driving force. As a result, flow characteristics are generally a result of one or more of the channel geometries, e.g., cross section and length which impact fluidic resistance through such channels, fluid the properties within the various channel segments, e.g., viscosity, and the like. While not providing for individual flow control within separate channel segments of the device, it will be appreciated that one can program flow rates into a channel structure through the design of the channel network, e.g., by providing varied channel dimensions to impact flow rates under a given driving force. Additionally, use of a single vacuum source coupled to the outlet of the channel network provides advantages of simplicity in having only a single driving force applied to the system.

In alternative or additional aspects, other fluid driving mechanisms may be employed, including for example, driving systems that are at least partially integrated into the fluid channels themselves, such as electrokinetic pumping structures, mechanically actuated pumping systems, e.g., diaphragm pumps integrated into the fluidic structures, centrifugal fluid driving, e.g., through rotor based fluidic components that drive fluid flow outward from a central reservoir through a radially extending fluidic network, by rapidly spinning the rotor, or through capillary force or wicking driving mechanisms.

The pump(s) are typically interfaced with the channel structures by a sealed junction between the pump, or conduit or manifold connected to the pump, and a terminus of the particular channel, e.g., through a reservoir or other interfacing component. In particular, with respect to the device illustrated in FIG. 2, a pump outlet may be interfaced with the channel network by mating the pump outlet to the opening of the reservoir with an intervening gasket or sealing element disposed between the two. The gasket may be an integral part of the microfluidic structure, the pump outlet, or both, or it may be a separate component that is placed between the microfluidic structure and the pump outlet. For example, an integrated gasket element may be molded over the top layer of the microfluidic device, e.g., as the upper surface of the reservoirs, as a second deformable material, e.g., a thermoplastic elastomer molded onto the upper lip of the reservoir that is molded from the same rigid material as the underlying microfluidic structure. Although described with reference to pressed interfaces of pump outlets to reservoirs on microfluidic devices, it will be appreciated that a variety of different interface components may be employed, including any of a variety of different types of tubing couplings (e.g., barbed, quick connect, press fit, etc.) to interface pressure sources to channel networks. Likewise, the pressure sources may be interfaced to upstream or downstream process components and communicated to the channel networks through appropriate interface components between the fluidic component in the partitioning system and the upstream or downstream process component. For example, where multiple integrated components are fluidically coupled together, application of a pressure to one end of the integrated fluidic system may be used to drive fluids through the conduits of each integrated component as well as to drive fluids from one component to another.

In some cases, both positive and negative pressures may be employed in a single process run. For example, in some cases, it may be desirable to process a partitioning run through a microfluidic channel network. Upon conclusion of the run, it may be desirable to reverse the flow through the device, to drive some portion of the excess non-aqueous component back out of the outlet reservoir back through the channel network, in order to reduce the amount of the non-aqueous phase that will be present in the outlet reservoir when being accessed by the user. In such cases, a pressure may be applied in one direction, either positive or negative, during the partitioning run to create the droplets through the microfluidic device, e.g., device 200 in FIG. 2, that accumulate in reservoir 238 along with excess non-aqueous phase material, which will remain at the bottom of the reservoir, e.g., at the interface with the channel 228. By then reversing the direction of pressure, either positive or negative, one may drive excess non-aqueous material back into the channel network, e.g., channel 228.

Additional control elements may be included coupled to the pumps of the system, including valves that may be integrated into manifolds, for switching applied pressures as among different channel segments in a single fluidic structure or between multiple channel structures in separate fluid components. Likewise, control elements may also be integrated into the fluidics components. For example, valving structures may be included within the channel network to controllably interrupt flow of fluids in or through one or more channel segments. Examples of such valves include the passive valves described above, as well as active controllable valve structures, such as depressible diaphragms or compressible channel segments, that may be actuated to restrict or stop flow through a given channel segment.

Figure 3A:
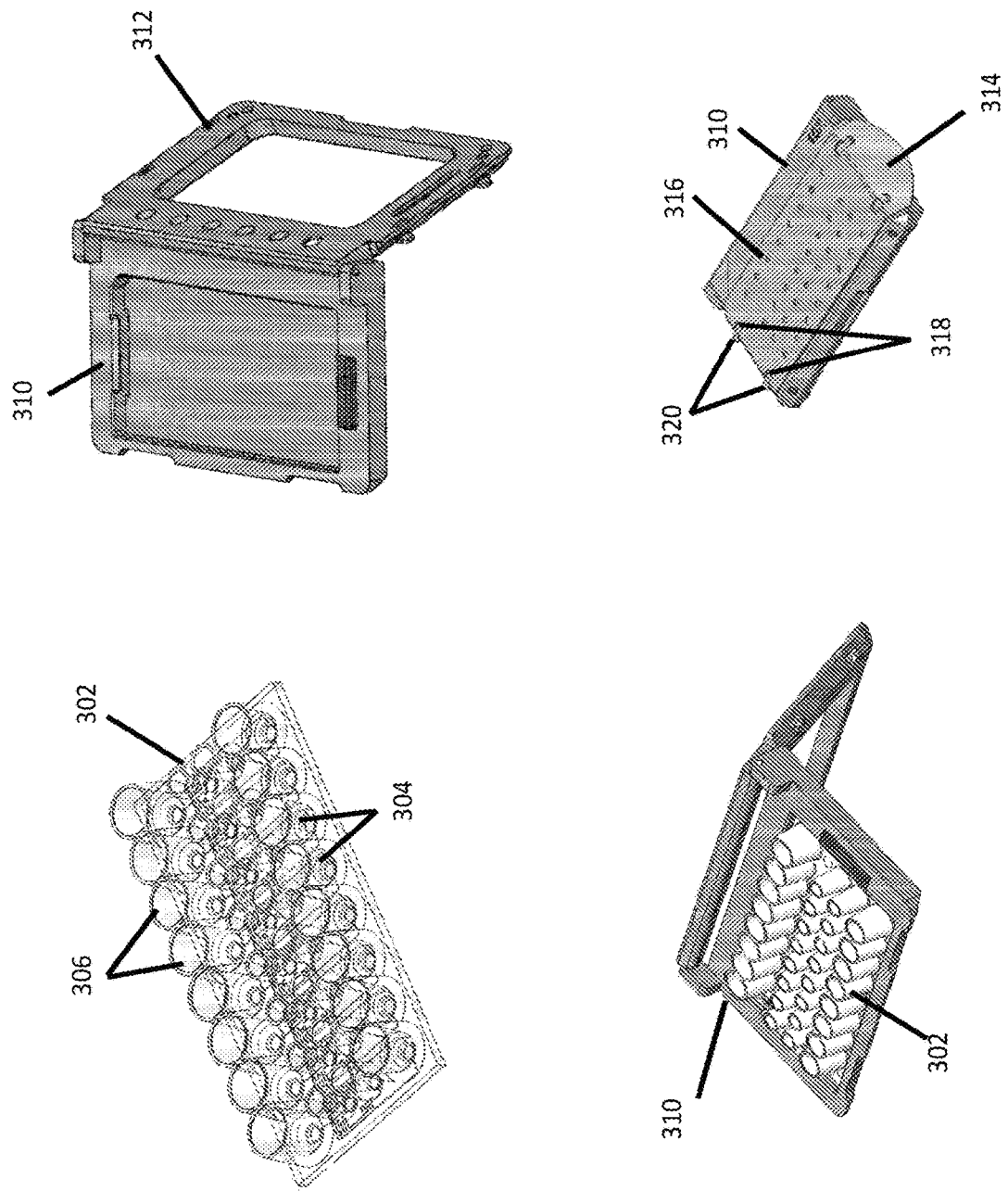
FIGS. 3A, 3B, and 3C illustrate different components of a microfluidic control system.
Figure 3B:
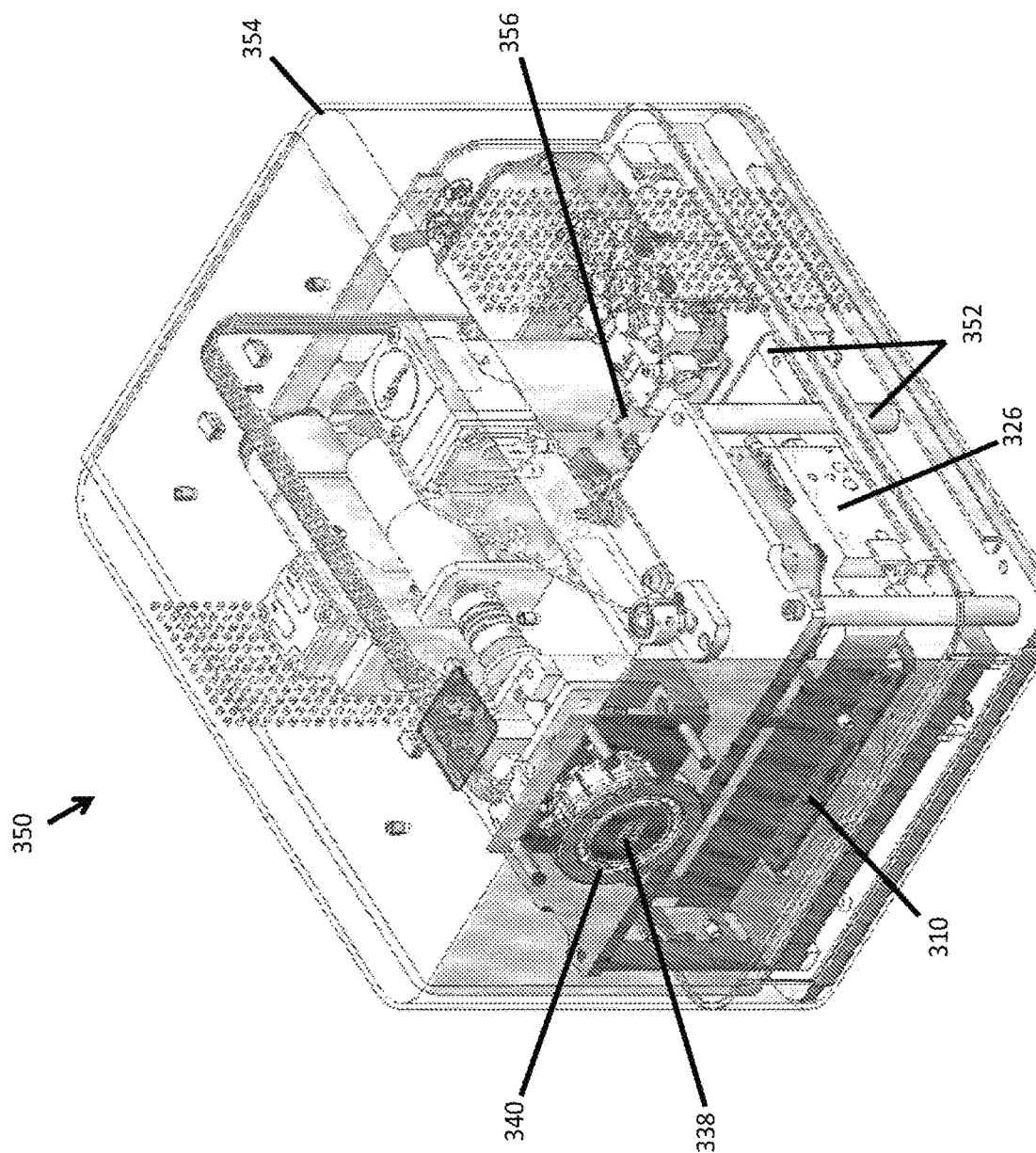
Figure 3C:
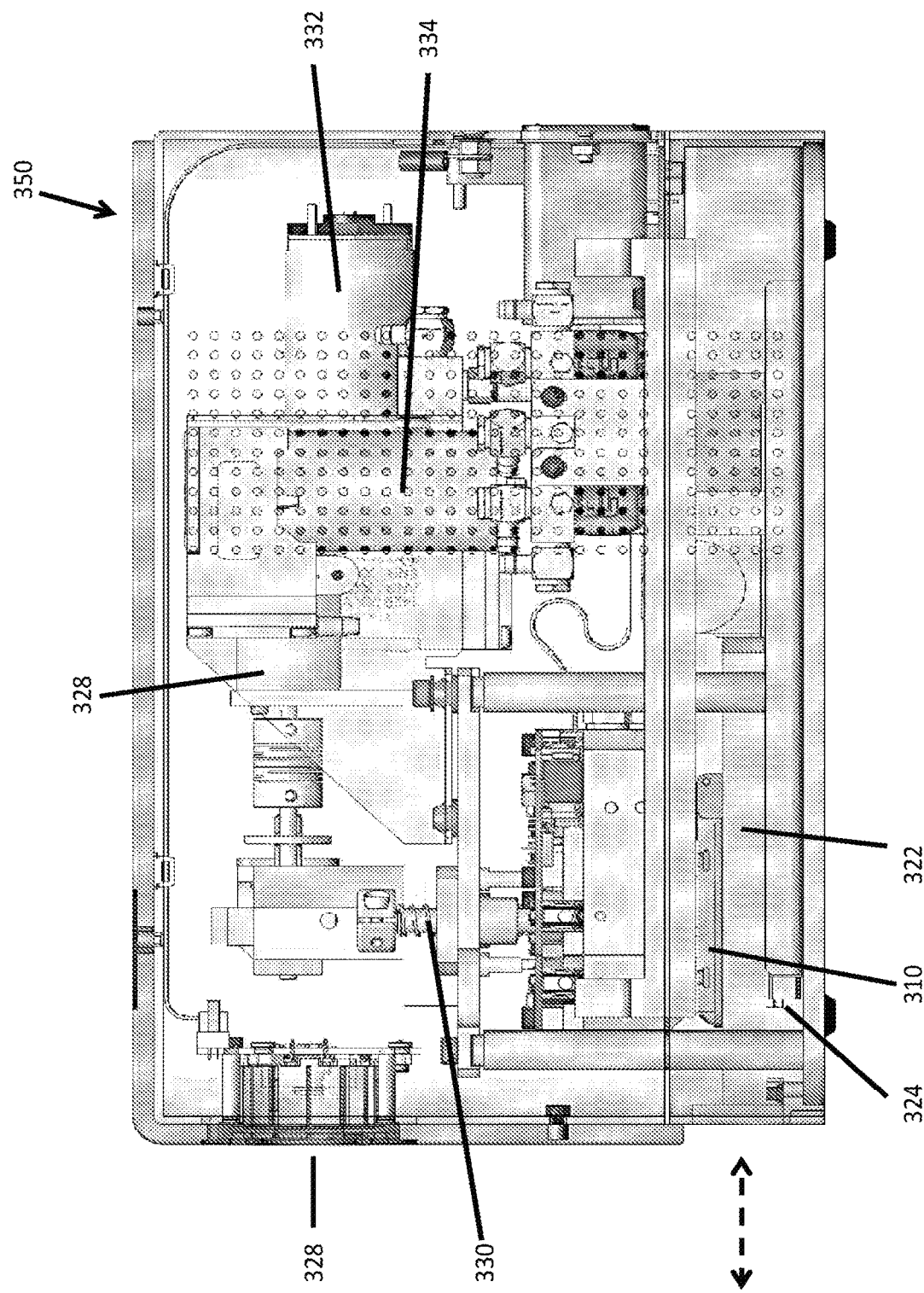

FIGS. 3A-3C illustrate components of an exemplary instrument/system architecture for interfacing with microfluidic components, as described above. As shown in FIG.

3A, a microfluidic device 302 that includes multiple parallel channel networks all connected to various inlet and outlet reservoirs, e.g., reservoirs 304 and 306, is placed into a secondary holder 310 that includes a closeable lid 312, to secure the device within the holder. Once the lid 312 is closed over the microfluidic device 302 in the secondary holder 310, an optional gasket 314 may be placed over the top of the reservoirs, e.g., reservoirs 304 and 306, protruding from the top of the secondary holder 310. As shown, gasket 314 includes apertures 316 to allow pressure communication between the reservoirs, e.g., reservoirs 304 and 306, and an interfaced instrument, through the gasket. As shown, gasket 314 also includes securing points 318 that are able to latch onto complementary hooks or other tabs 320 on the secondary holder to secure the gasket 314 in place. Also as shown, secondary holder 310 is assembled such that when the lid portion 312 is fully opened, it creates a stand for the secondary holder 310 and a microfluidic device, e.g., microfluidic device 302, contained therein, retaining the microfluidic device 302 at an appropriate orientation, e.g., at a supported angle, for recovering partitions or droplets generated within the microfluidic device 302. Typically, the supported angle at which the microfluidic device 302 is oriented by the lid 312 will range from about 20-70 degrees, more typically about 30-60 degrees, preferably 40-50 degrees, or in some cases approximately 45 degrees. Though recited in terms of certain ranges, it will be understood that all ranges from the lowest of the lower limits to the highest of the upper limits are included, including all intermediate ranges or specific angles, within this full range or any specifically recited range. Such angles provide an improved or optimized configuration for recovering the partitions or droplets generated within the microfluidic device 302 while minimizing or preventing spillage of the fluids within the microfluidic device 302.

FIG. 3B shows a perspective view of an instrument system 350 while FIG. 3C illustrates a side view of the instrument system 350. As shown, and with reference to FIG. 3A, a microfluidic device 302 may be placed into a secondary holder 310 that is, in turn, placed upon a retractable tray 322, that moves is slidable into and out of the instrument system 350. The retractable tray 322 is positioned on guide rails 324 that extend in a horizontal direction of the instrument system 350 (as shown by the arrows in FIG. 3C) and allow the retractable tray 322 to slide into and out of a slot formed in the housing 354 when driven by a driving mechanism. In some embodiments, the driving mechanism may include a motor part (not shown) to transmit rotation power, and a moving link part (not shown) extending from the motor part towards the guide rails 324, such that the moving link part is connected to the guide rails 324 to slide the guide rails 324 in the horizontal direction when the motor part is operated. Pinion gears (not shown) may be formed on the moving link part and rack gears (not shown) extending in the horizontal direction may be formed on the guide rails 324 such that the pinion gears are engaged with the rack gears, and when the motor part is operated, the moving link part is rotated and the pinion gears are rotated and moved along the rack gears to slide the retractable tray 322, positioned on the guide rails 324, into and out of the housing 354.

Once secured within the instrument system 350, a depressible manifold assembly 326 is lowered into contact with the reservoirs, e.g., reservoirs 304 and 306 in the microfluidic device 302, making sealed contact between the manifold assembly 326 and the reservoirs 304 and 306 by virtue of intervening gasket 314. Depressible manifold assembly 326 is actuated and lowered against the microfluidic device 302 through incorporated servo motor 328 that controls the movement of the manifold assembly 326, e.g., through a rotating cam (not shown) that is positioned to push the manifold assembly 326 down against microfluidic device 302 and gasket 314, or through another linkage. The manifold assembly 326 is biased in a raised position by springs 330. Once the manifold assembly 326 is securely interfaced with the reservoirs, e.g., reservoirs 304 and 306, on the microfluidic device 302, pressures are delivered to one or more reservoirs, e.g., reservoirs 304 and 306, within each channel network within the microfluidic device 302, depending upon the mode in which the system is operating, e.g., pressure or vacuum drive. The pressures are supplied to the appropriate conduits within the manifold 326 from one or both of pumps 332 and 334. Operation of the system is controlled through onboard control processor, shown as circuit board 356, which is programmed to operate the pumps in accordance with preprogrammed instructions, e.g., for requisite times or to be responsive to other inputs, e.g., sensors or user inputs. Also shown is a user button 338 that is depressed by the user to execute the control of the system, e.g., to extend and retract the tray 322 prior to a run, and to commence a run. Indicator lights 340 are provided to indicate to the user the status of the instrument and/or system run. The instrument components are secured to a frame 352 and covered within housing 354.

IV. Environmental Control

In addition to flow control components, the systems described herein may additionally or alternatively include other interfaced components, such as environmental control components, monitoring components, and other integrated elements.

In some cases, the systems may include environmental control elements for controlling parameters in which the channel networks, reagent vessels, and/or product reservoirs are disposed. In many cases, it will be desirable to maintain controlled temperatures for one or more of the fluidic components or the elements thereof. For example, when employing transient reactants, it may be desirable to maintain cooler temperatures to preserve those reagents. Likewise, in many cases partitioning systems may operate more optimally at a set temperature, and maintaining the system at such temperature will reduce run-to-run variability. Temperature controllers may include any of a variety of different temperature control systems, including simple heaters and coolers, fans or radiators, interfaced with the fluidics component portion of the system. In preferred aspects, temperature control may be provided through a thermoelectric heater/cooler that is directly contacted with the device, or a thermal conductor that is contacted with the device, in order to control its temperature. Thermoelectric coolers are widely available and can generally be configured to apply temperature control to a wide variety of different structures and materials. The temperature control systems will typically be included along with temperature sensing systems for monitoring the temperature of the system or key portions of it, e.g., where the fluidics components are placed, so as to provide feedback control to the overall temperature control system.

In addition to temperature control, the systems may likewise provide control of other environmental characteristics, such as providing a controlled humidity level within the instrument, and/or providing a light or air sealed environment, e.g., to prevent light damage or potential contamination from external sources.

V. Monitoring and Detection

The systems described herein also optionally include other monitoring components interfaced with the fluidics components. Such monitoring systems include, for example, pressure monitoring systems, level indicator systems, e.g., for monitoring reagent levels within reservoirs, and optical detection systems, for observing fluids or other materials within channels within the fluidics components.

A. Pressure

A variety of different monitoring systems may be included, such as pressure monitoring systems that may allow identification of plugged channels, air bubbles, exhaustion of one or more reagents, e.g., that may signal the completion of a given operation, or real time feedback of fluid flows, e.g., indicating viscosity by virtue of back pressures, etc. Such pressure monitoring systems may often include one or more pressure sensors interfaced with one or more fluidic channels, reservoirs or interfacing components, e.g., within the lines connecting the pumps to the reservoirs of the device, or integrated into other conduits coupled to other reservoirs. By way of example, where a positive pressure is applied to multiple inlet reservoirs, pressure sensors coupled to those inlet reservoirs can allow the detection of a channel clog which may be accompanied by a pressure increase, or injection of air through a channel which may accompany exhaustion of one or more reagents from a reservoir, which may be accompanied by a pressure drop. Likewise, pressure sensors coupled to a reservoir to which a negative pressure is applied may similarly identify perturbations in pressure that may be indicative of similar failures or occurrences. With reference to FIG. 1, pressure sensors may be optionally integrated into one or more of the lines connecting the pumps 118-128 (shown as dashed lines), or integrated directly into the reservoirs 106-116, disposed at the termini of the various channel segments in the fluidic channel network 104. The sensors incorporated into the instrument may typically be operably coupled to the controller that is integrated into the instrument, e.g., on circuit board 356 shown in FIG. 3B. Alternatively or additionally, the sensors may be linked, e.g., through appropriate connectors, to an external processor for recording and monitoring of signals from those sensors.

As will be appreciated, when in normal operation, it would be expected that the pressure profiles at the one or more sensors would be expected to remain relatively steady. However, upon a particular failure event, such as aspiration of air into a channel segment, or a blockage at one or more channel segments or intersections, would be expected to cause a perturbation in the steady state pressure profiles. For example, for a system as shown in FIG. 1, that includes an applied negative pressure at an outlet reservoir, e.g., reservoir 116 with an integrated pressure sensor, normal operation of the system would be expected to have a relatively steady state of this negative pressure exhibited at the reservoir. However, in the event of a system disturbance, such as exhaustion of a reagent in one or more of reservoirs 106-114, and resulting aspiration of air into the channels of the system, one would expect to see a reduction in the negative pressure (or an increase in pressure) at the outlet reservoir resulting from the sudden decrease in fluidic resistance in the channel network resulting from the introduction of air. By monitoring the pressure profile, the system may initiate changes in operation in response to such perturbations, including, e.g., shut down of the pumps, triggering of alarms, or other measures, in order to void damaging failure events, e.g., to the system or the materials being processed therein. As will be appreciated, pressure profiles would be similarly monitorable when using individually applied pressures at multiple reservoirs/channel termini. For example, for positive applied pressures, introduction of air into channels would be expected to cause a drop in pressure at an inlet reservoir, while clogs or obstructions would be expected to result in increases in pressures at the inlets of a given clogged channel or channels.

In some cases, one or more pressure sensors may be integrated within the manifold or pressure lines that connect to one or more of the reservoirs or other channel termini, as described herein. A variety of pressure sensor types may be integrated into the systems described herein. For example, small scale solid state pressure sensors may be coupled, in-line, with pressure or vacuum lines connected to the reservoirs of the fluidic components, in order to measure pressure within those lines and at those reservoirs. As with the pumps described herein, pressure sensors may be integrated with one or more of the reservoirs, including the outlet and inlet reservoirs, as applicable. In some cases, each pressure conduit connected to a reservoir within a device may include a pressure sensor for monitoring pressures at such reservoirs.

In operation, the pressure sensing system is used to identify pressure perturbations that signal system failures or end-of-run events, such as channel clogs, air aspiration through channels, e.g., from reagent exhaustion, or the like. In particular, the pressure sensing system is used to trigger system operations when the steady state pressures measured by the pressure sensing system deviate above or below a threshold amount. Upon occurrence of such a perturbation, the system may be configured to shut down, or reduce applied pressures, or initiate other mitigation measures to avoid adulterating the overall system, e.g., by drawing fluids into the pumping system, or manifold. In certain aspects, the system will be configured to shut down or reduce applied pressures when the steady state pressure measured in one or more channel segments deviates from the steady state pressure by more than 10%, more than 20%, more than 30%, more than 40%, more than 50%, more than 60%, or more.

In addition to or as an alternative to the pressure sensors described above, one or more flow sensors may also be integrated into the system, e.g., within the manifold or flow lines of the system, in order to monitor flow through the monitored conduit. As with the pressure sensors, these flow sensors may provide indications of excessive flow rates within one or more of the conduits feeding the fluidic device, as well as provide indications of perturbations in that flow resulting from system problems or fluidics problems, e.g., resulting from channel occlusions or constrictions, exhaustion of one or more fluid reagents, etc.

B. Optical Monitoring and Detection

In addition to pressure sensors, the systems described herein may also include optical sensors for measurement of a variety of different parameters within the fluid components of the system, as well as within other parts of the system. For example, in at least one example, an optical sensor is positioned within the system such that it is in optical communication with one or more of the fluid channels in the fluid component. The optical sensor is typically positioned adjacent one or more channels in the fluid component, so that it is able to detect the passage of material through the particular channel segment. The detection of materials may be by virtue of the change in optical properties of the fluids flowing through the channel, e.g., light scattering, refractive index, or by virtue of the presence of optically detectable species, e.g., fluorophores, chromophores, colloidal materials, or the like, within the fluid conduits.

In many cases, the optical detection system optionally includes one or more light sources to direct illumination at the channel segment. The directed light may enhance aspects of the detection process, e.g., providing contrasting light or excitation light in the illumination of the contents of the channel. In some cases, the light source may be an excitation light source for exciting fluorescent components within the channel segment that will emit fluorescent signals in response. These fluorescent signals are then detected by the optical sensor.

Figure 4:
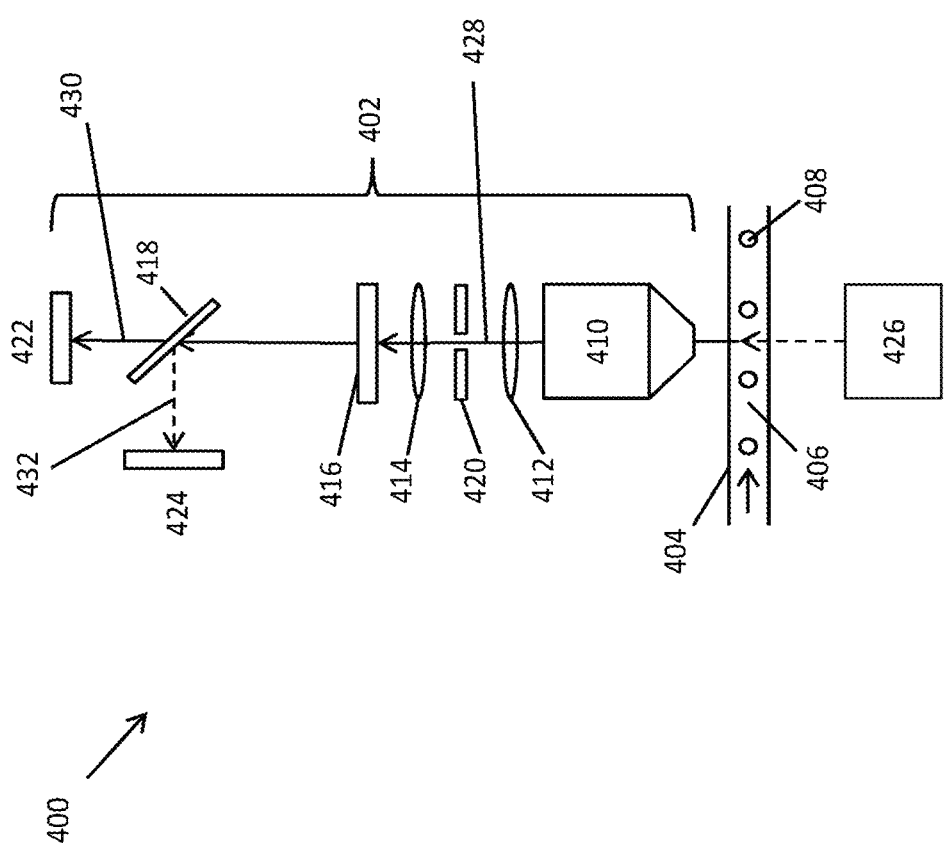
FIG. 4 schematically illustrates the structure of an example optical detection system for integration into overall instrument systems described herein.

FIG. 4 schematically illustrates an example of an optical detection system for monitoring materials within fluidic channels of the fluidics component of the systems described herein. As shown, the optical detection system 400 typically includes an optical train 402 placed in optical communication with one or more channel segments within the fluidic component, e.g., channel segment 404. In particular, optical train 402 is placed within optical communication with channel segment 404 in order to optically interrogate the channel segment and/or its contents, e.g., fluid 406 and particles or droplets 408. Generally, the optical train will typically include a collection of optical components used for conveying the optical signals from the channel segments to an associated detector or detectors. For example, optical trains may include an objective lens 410 for receiving optical signals from the fluid channel 404, as well as associated optical components, e.g., lenses 412 and 414, spectral filters and dichroics 416 and 418, and spatial filters, e.g., filter 420, for directing those optical signals to a detector or sensor 422 (and one or more optional additional sensors, e.g., sensor 424), such as a CCD or CMOS camera, PMT, photodiode, or other light detecting device.

In some cases, the optical detection system 400 may operate as a light microscope to detect and monitor materials as they pass through the channel segment(s) in question. In such cases, the optical train 402 may include spatial filters, such as confocal optics, e.g., filter 420, as well as an associated light source 426, in order to increase contrast for the materials within the channel segment.

In some cases, the optical detection system may alternatively, or additionally be configured to operate as a fluorescence detection microscope for monitoring fluorescent or fluorescently labeled materials passing through the channel segments. In the case of a fluorescence detection system, light source 426 may be an excitation light source, e.g., configured to illuminate the contents of a channel at a wavelength that excites fluorescence from the materials within the channel segment. In such cases, the optical train 402, may additionally be configured with filter optics to allow the detection of fluorescent emissions from the channel without interference from the excitation light source 426. This is typically accomplished through the incorporation of cut-off or narrow band pass filters, e.g., filter 416 within the optical train to filter out the excitation wavelength while permitting light of the wavelengths emitted by the fluorescent species to pass and be detected.

In particularly preferred aspects, the optical sensor is provided optically coupled to one or more of a particle inlet channel segment (through which beads or other particles are injected into the partitioning region of the fluidic component of the system), e.g., channel segment 202 of FIG. 2, to monitor the materials being brought into the partitioning junction, e.g., monitoring the frequency and flow rates of particles that are to be co-partitioned in the partitioning junction. Alternatively or additionally, the optical detector may be positioned in optical communication with the post partitioning channel segment of the fluidic component, e.g., channel segment 228, to allow the monitoring of the formed partitions emanating from the partitioning junction of the fluidic device or structure. In particular, it is highly desirable to be able to monitor and maintain control of the flow of particles that are being introduced into the partitioning region, and to monitor and control the flow and characteristics of partitions as they are being generated in order to ensure the proper flow rates and generation frequencies for the partitions, as well as to understand the efficiency of the partitioning process.

In a particular example, the optical sensor is used to monitor and detect partitions as they pass a particular point in the channel segment. In such cases, the optical sensor may be used to measure physical characteristics of the partitions, or their components, as they pass the position in the channel, such as the size, shape, speed or frequency of the partitions as they pass the detector. In other cases, the optical detector or sensor 422 may be configured to detect some other characteristics of the partitions as they pass the detector or sensor 422, e.g., relating to the contents of the partitions.

As noted above, in some cases, the optical detection system will be configured to monitor aspects of the contents of the created partitions. For example, in some cases, materials that are to be co-partitioned into individual partitions may be monitored to detect the relative ratio of the co-partitioned materials. By way of example, two fluid borne materials, e.g., a reagent, and a bead population, may each be differentially optically labeled, and the optical detection system is configured to resolve the contribution of these materials in the resulting partitions.

In an example system, two optically resolvable fluorescent dyes may be separately suspended into each of the first reagent and the second reagents that are to be co-partitioned. The relative ratio of the first and second reagents in the resulting partition will be ascertainable by detecting the fluorescent signals associated with each fluorescent dye in the resulting partition. Accordingly, the optical detection system will typically be configured for at least two-color fluorescent optics. Such two color systems typically include one or more light sources that provide excitation light at the appropriate wavelengths to excite the different fluorescent dyes in the channel segment. These systems also typically include optical trains that differentially direct the fluorescent emissions from those dyes to different optical detectors or regions on the same detector. With reference to FIG. 4, for example, two optically distinguishable fluorescent dyes may be co-partitioned into droplets, e.g., droplets 408 within channel segment 404. Upon excitation of those fluorescent dyes by light source 426, two optically resolvable fluorescent signals are emitted from the droplets 408, shown as solid arrow 428. The mixed fluorescent signals, along with transient excitation light are collected through objective 410 and passed through optical train 402. Excitation light is filtered out of the signal path by inclusion of an appropriate filter, e.g., filter 416, which may include one or more cut-off or notch filters that pass the fluorescent light wavelengths while rejecting the excitation wavelengths. The mixed fluorescent signals are then directed toward dichroic mirror 420, which allows one of the fluorescent signals (shown by arrow 430) to pass through to a first detector 422, while reflecting a second, spectrally different fluorescent signal (shown by arrow 432), to second detector 424.

The intensities of each fluorescent signals associated with each dye, are reflective of the concentration of those dyes within the droplets. As such, by comparing the ratio of the signal from each fluorescent dye, one can determine the relative ratio of the first and second fluids within the partition. Further, by comparing the detected fluorescence to known extinction coefficients for the fluorescent dyes, as well as the size of observed region, e.g., a droplet, one can determine the concentration of each component within a droplet. As will be appreciated, where looking to partition particle based reagents into droplets, when using a fluorescently labeled particle, these systems also will allow one to ascertain the relative number of particles within a partition, as well as identifying partitions that contain no particles.

Figure 5:
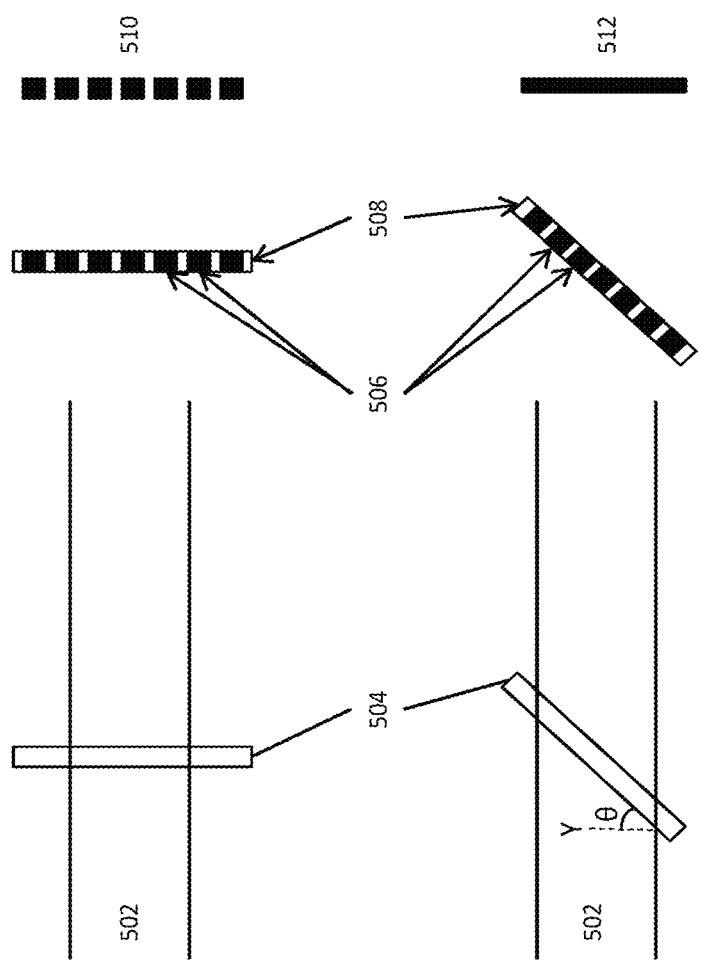
FIG. 5 schematically illustrates an alternate detection scheme for use in imaging materials within microchannels.

In other aspects, the optical detection systems may be used to determine other characteristics of the materials, particles, partitions or the like, flowing through the channel segments, including, for example, droplet or particle size, shape, flow rate, flow frequency, and other characteristics. In at least one aspect, optical detectors provided are configured to better measure these characteristics. In one aspect, this is achieved through the incorporation of a line scan camera or detector, e.g., camera 510, into the optical system, that images across a channel segment in a detection line in order to process images of the materials as they pass through the detection line. This is schematically illustrated in FIG. 5, top panel. As shown, a channel segment 502 is provided wherein materials, and particularly particulate or droplet based materials are being transported. The optical detection system images a line across the channel segment 502 (indicated as image zone 504). Because the line scan camera employs a line scanner, rather than a two-dimensional array of pixels associated with other camera types, it results in substantially less image processing complexity, allowing greater flexibility of operation.

In addition to using a line scan camera system, in some cases, it is desirable to provide higher resolution imaging using such camera systems by angling the detection line across the channel segment 502, as shown in FIG. 5, bottom panel. In particular, assuming a linear, one-dimensional array of pixels in a line scan camera (schematically illustrated as pixels 506 in camera 508), one would expect an image that is reflective of those pixels (schematically illustrated as image 510). Typically, the angle θ at which the detection line (indicated as image zone 504) is angled across the channel segment 502 will range from about 5-80 degrees from an axis Y perpendicular to the channel segment 502, more specifically 15-75 degrees, 20-70 degrees, 25-65 degrees, 30-60 degrees, 35-55 degrees, 40-50 degrees, or in some cases approximately 45 degrees. Though recited in terms of certain ranges, it will be understood that all ranges from the lowest of the lower limits to the highest of the upper limits are included, including all intermediate ranges or specific angles, within this full range or any specifically recited range. By angling the camera and the detection line/image zone 504, one achieves an effective closer spacing of the pixels as they image flowing materials. The resulting image thus is of higher resolution across the channel, as shown by image 512, than for the perpendicularly oriented image zone, as shown by image 510. By providing higher resolution, one is able to obtain higher quality images of the particles, droplets or other materials flowing through the channel segments of the device, and from that, derive the shape, size and other characteristics of these materials.

As will be appreciated, as the optical detection systems may be used to monitor flow rates within channel segments of a device, these detection systems may, as with the pressure monitoring systems described above, identify perturbations in the operation of the system. For example, where a reagent well is exhausted, allowing air to be passed through the channels of the device, while leading to a pressure drop across the relevant channel segments, it will also result in an increase in flow rate through that channel segment resulting from the lower fluidic resistance in that channel. Likewise, an obstructed channel segment will in many cases, lead to a reduced flow rate in downstream channel segments connected to the obstructed channel segment. As such, perturbations in flow rates measured optically, may be used to indicate system failures or run completions or the like. In general, perturbations of at least 5% in the optically determined flow rate, at least 10%, at least 20%, at least 30%, at least 40%, or at least 50%, will be indicative of a problem during a processing run, and may result in a system adjustment, shutdown or the like.

Figure 8:
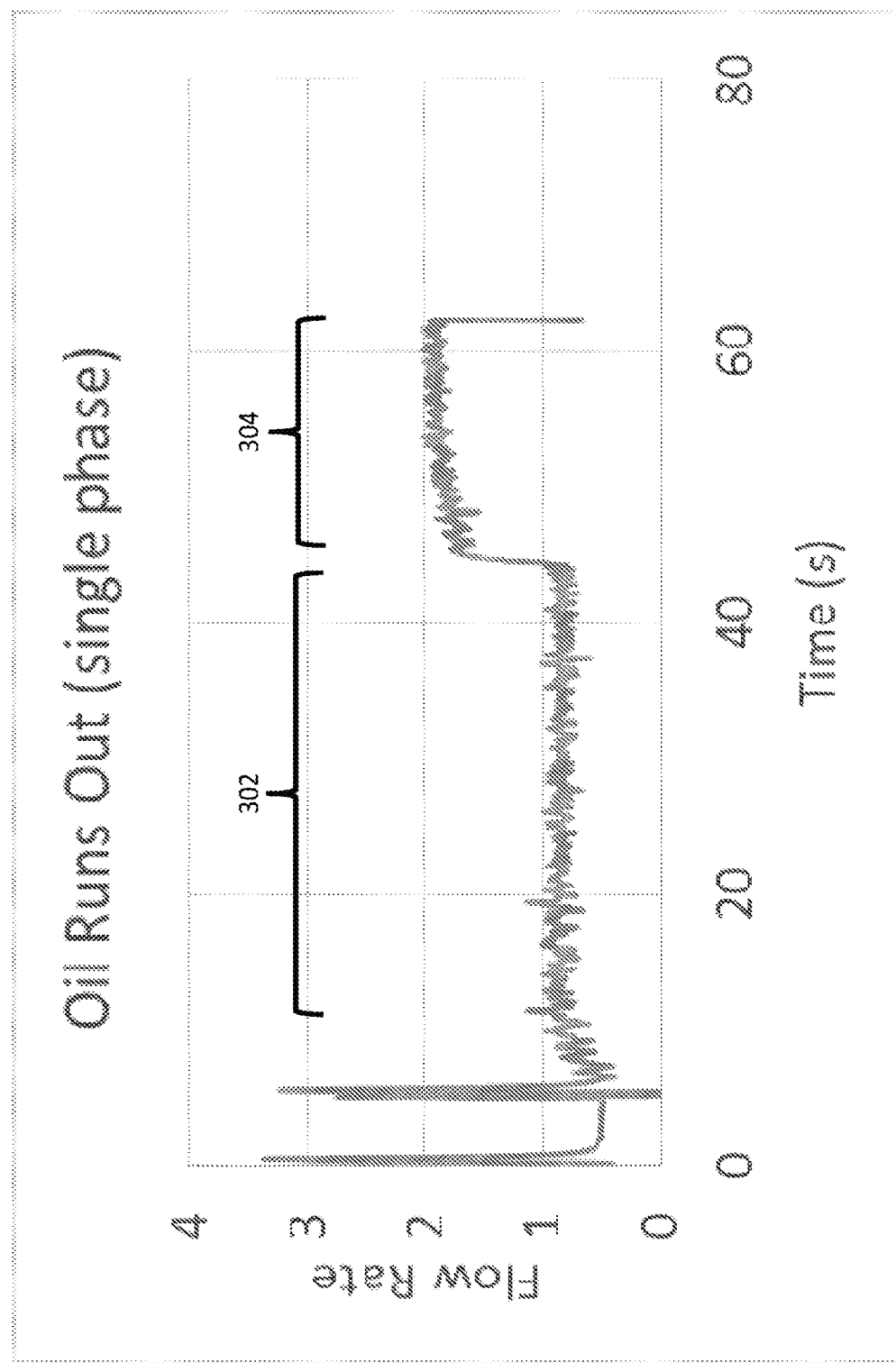
FIG. 8 illustrates a monitored pressure profile across a microfluidic channel network for use in controlling fluidic flows through the channel network.

FIG. 8 illustrates optical monitoring processes and systems as described herein for use in identifying perturbations in flow within channels of a fluidic network. As shown, a single a microfluidic device, e.g., as shown in FIG. 2, is run under applied pressures at each of the various inlet reservoirs, e.g., reservoirs 230, 232 and 234, under constant pressure. The flow rate of droplets is measured within an outlet channel segment, e.g., channel segment 228 using an optical imaging system. The flow rate of a normally operating channel segment is plotted in the first portion 302 of the flow rate plot shown in FIG. 8. Upon exhaustion of one reagent, e.g., the oil in reservoir 234, air is introduced into the channel network, resulting in a reduced fluidic resistance, causing an increase in the flow rate, as shown in the second portion 304 of the plot.

VI. Reagent Detection

In addition to the components described above, in some cases, the overall systems described herein may include additional components integrated into the system, such components used to detect the presence and amount of reagents present in any reagent vessel component of the system, e.g., in a reservoir of a microfluidic device, an amplification tube, or the like. A variety of components may be used to detect the presence and/or amount of reagents in any vessel, including, for example, optical detection systems, that could include light transmission detectors that measure whether light is altered in passing through a reservoir based upon presence of a fluid, or machine vision systems that image the reservoirs and determine whether there is fluid in the reservoir and even the level of fluid therein. Such detection systems would be placed in optical communication with the reservoirs or other vessels of the system. In other cases, electrical systems may be used that insert electrodes into a reservoir and measure changes in current flow through those electrodes based upon the presence or absence of fluid within the reservoir or vessel.

VII. Additional Sensors/Monitoring

In addition to the sensing systems described above, a number of additional sensing systems may also be integrated into the overall systems described herein. For example, in some cases, the instrument systems may incorporate barcode reader systems in one or more functional zones of the system. For example, in some cases, a barcode reader may be provided adjacent a stage for receiving one or more sample plates, in order to record the identity of the sample plat and correlate it to sample information for that plate. Likewise, barcode readers may be positioned adjacent a microfluidic device stage in a partitioning zone, in order to record the type of microfluidic device being placed on the stage, as reflected by a particular barcode placed on the device. By barcoding and reading the specific device, one could coordinate the specifics of an instrument run that may be tailored for different device types. A wide variety of barcode types and readers are generally used in research instrumentation, including both one dimensional and two dimensional barcode systems.

Other detection systems that are optionally integrated into the systems described herein include sensors for the presence or absence of consumable components, such as microfluidic devices, sample plates, sample tubes, reagent tubes or the like. Typically, these sensor systems may rely on one or more of optical detectors, e.g., to sense the presence or absence of a physical component, such as a plate, tube, secondary holder, microfluidic chip, gasket, etc., or mechanical sensors, e.g., that are actuated by the presence or absence of a plate, microfluidic device, secondary holder, tube, gasket, etc. These sensor systems may be integrated into one or more tube slots or wells, plate stages or microfluidic device stages. In the event a particular component is missing, the system may be programmed to provide an alert or notification as well as optionally or additionally preventing the start of a system run or unit operation.

II. Integrated Workflow Processes

The instrument systems described above may exist as standalone instruments, or they may be directly integrated with other systems or subsystems used in the particular workflow for the application for which the partitioning systems are being used. As used herein, integration of systems and subsystems denotes the direct connection or joining of the systems and/their respective processes into an integrated system or instrument architecture that does not require user intervention in moving a processed sample or material from a first subsystem to a second subsystem. Typically, such integration denotes two subsystems that are linked into a common architecture, and include functional interactions between those subsystems, or another subsystem common to both. By way of example, such interconnection includes exchage of fluid materials from one subsystem to another, exchange of components, e.g., plates, tubes, wells, microfluidic devices, etc., between two subsystems, and additionally, may include integrated control components between subsystems, e.g., where subsystems are controlled by a common processor, or share other common control elements, e.g., environment control, fluid transport systems, etc.

For ease of discussion, these integrated systems are described with respect to the example of nucleic acid applications. In this example, the partitioning instrument systems may be integrated directly with one or more sample preparation systems or subsystems that are to be used either or both of upstream and/or downstream in the specific overall workflow. Such systems may include, for example, upstream process systems or subsystems, such as those used for nucleic acid extraction, nucleic acid purification, and nucleic acid fragmentation, as well as downstream processing systems, such as those used for nucleic acid amplification, nucleic acid purification and nucleic acid sequencing or other analyses.

For purposes of illustration, the integration of the partitioning process components described above, with upstream and/or downstream process workflow components is illustrated with respect to a preferred exemplary nucleic acid sequencing workflow. In particular, the partitioning systems described herein are fluidly and/or mechanically integrated with other systems utilized in a nucleic acid sequencing workflow, e.g., amplification systems, nucleic acid purification systems, cell extraction systems, nucleic acid sequencing systems, and the like.

Figure 6:
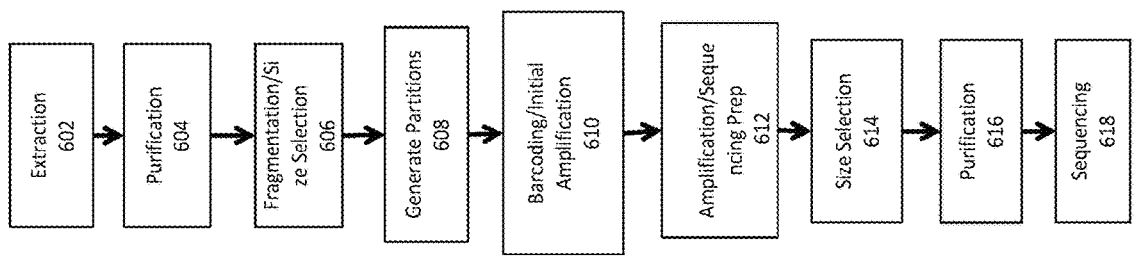
FIG. 6 illustrates an exemplary processing workflow, some or all of which may be integrated into a unified system architecture.

FIG. 6 schematically illustrates an exemplary process workflow for sequencing nucleic acids from sample materials and assembling the obtained sequences into whole genome sequences, contig sequences, or sequences of significantly large portions of such genomes, e.g., fragments of 10 kb or greater, 20 kb or greater, 50 kb or greater, or 100 kb or greater, exomes, or other specific targeted portions of the genome(s).

As shown, a sample material, e.g., comprising a tissue or cell sample, is first subjected to an extraction process 602 to extract the genomic or other nucleic acids from the cells in the sample. A variety of different extraction methods are commercially available and may vary depending upon the type of sample from which the nucleic acids are being extracted, the type of nucleic acids being extracted, and the like. The extracted nucleic acids are then subjected to a purification process 604, to remove extraneous and potentially interfering sample components from the extract, e.g., cellular debris, proteins, etc. The purified nucleic acids may then be subjected to a fragmentation step 606 in order to generate fragments that are more manageable in the context of the partitioning system, as well as optional size selection step, e.g., using a SPRI bead clean up and size selection process.

Following fragmentation, the sample nucleic acids may be introduced into the partitioning system, which is used to generate the sequenceable library of nucleic acid fragments. Within the partitioning system larger sample DNA fragments are co-partitioned at step 608, along with barcoded primer sequences, such that each partition includes a particular set of primers representing a single barcode sequence. Additional reagents may also be co-partitioned along with the sample material, including, e.g., release reagents for releasing the primer/barcode oligonucleotides from the beads, DNA polymerase enzyme, dNTPs, divalent metal ions, e.g., Mg2+, Mn2+, and other reagents used in carrying out primer extension reactions within the partitions. These released primers/barcodes are then used to generate a set of barcoded overlapping smaller fragments of the larger sample nucleic acid fragments at amplification step 610, where the smaller fragments include the barcode sequence, as well as one or more additional sequencing primer sequences.

Following generation of the sequencing library, additional process steps may be carried out prior to introducing the library onto a sequencer system. For example, as shown, the barcoded fragments may be taken out of their respective partitions, e.g., by breaking the emulsion, and be subjected to a further amplification process at step 612 where the sequenceable fragments are amplified using, e.g., a PCR based process. Either within this process step or as a separate process step, the amplified overlapping barcoded fragments may have additional sequences appended to them, such as reverse read sequencing primers, sample index sequences, e.g., that provide an identifier for the particular sample from which the sequencing library was created.

In addition, either after the amplification step (as shown) or prior to the amplification step, the overlapping fragment set may be size selected, e.g., at step 614, in order to provide fragments that are within a size nucleotide sequence length range that is sequenceable by the sequencing system being used. A final purification step 616 may be optionally performed to yield a sequenceable library devoid of extraneous reagents, e.g., enzymes, primers, salts and other reagents, that might interfere with or otherwise co-opt sequencing capacity of the sequencing system. The sequencing library of overlapping barcoded fragments is then run on a sequencing system at step 618 to obtain the sequence of the various overlapping fragments and their associated barcode sequences.

In accordance with the instant disclosure, it will be appreciated that the steps represented by the partitioning system, e.g., step 606, may be readily integrated into a unified system with any one or more of any of steps 602-606 and 610-618. This integration may include integration on the subsystem level, e.g., incorporation of adjacent processing systems within a unified system architecture. Additionally or alternatively, one or more of these integrated systems or components thereof, may be integrated at the component level, e.g., within one or more individual structural components of the partitioning subsystem, e.g., in an integrated microfluidic partitioning component.

As used herein, integration may include a variety of types of integration, including for example, fluidic integration, mechanical integration, control integration, electronic or computational integration, or any combination of these. In particularly preferred aspects, the partitioning instrument systems are fluidly and/or mechanically integrated with one or more additional upstream and/or downstream processing subsystems.

A. Fluidic Integration

In the case of fluidic integration, it will be understood that such integration will generally include fluid transfer components for transferring fluid components to or from the inlets and outlets, e.g., the reservoirs, of the fluidic component of the partitioning system. These fluid transfer components may include any of a variety of different fluid transfer systems, including, for example, automated pipetting systems that access and pipette fluids to or from reservoirs on the fluidic component to transfer such fluids to or from reservoirs, tubes, wells or other vessels in upstream or downstream subsystems. Such pipetting systems may typically be provided in the context of appropriate robotics within an overall system architecture, e.g., that move one or both of the fluidics component and/or the pipetting system relative to each other and relative to the originating or receiving reservoir, etc. Alternatively, such systems may include fluidic conduits that move fluids among the various subsystem components. Typically, hard wired fluidic conduits are reserved for common reagents, buffers, and the like, and not used for sample components, as they would be subject to sample cross contamination.

In one example, a fluid transfer system is provided for transferring one or more fluids into the reservoirs that are connected to the channel network of the fluidics component. For example, in some cases, fluids, such as partitioning oils, buffers, reagents, e.g., barcode beads or other reagents for a particular application, may be stored in discrete vessels, e.g., bottles, flasks, tubes or the like, within the overall system. These storage vessels would optionally be subject to environmental control aspects as well, to preserve their efficacy, e.g., refrigeration, low light or no light environments, etc.

Upon commencement of a system run, those reagent fluids would be transported to the reservoirs of a fluidic component, e.g., a microfluidic device, that was inserted into the overall system. Again, reagent transport systems for achieving this may include dispensing systems, e.g., with pipettors or dispensing tubes positioned or positionable over the reservoirs of the inserted device, and which are connected to the reagent storage vessels and include pumping systems.

Likewise, fluid transport systems may also be included to transfer the partitioned reagents from the outlet of the fluidic component, e.g., reservoir 238 in FIG. 2, and transported to separate locations within the overall system for subsequent processing, e.g., amplification, purification etc.

In other cases, the partitions may be maintained within the outlet reservoir of the fluidic component, which is then directly subjected to the amplification process, e.g., through a thermal controller placed into thermal contact with the outlet reservoir, that can perform thermal cycling of the reservoir's contents. This thermal controller may be a component of the mounting surface upon which the microfluidic device is positioned, or it may be a separate component that is brought into thermal communication with the microfluidic device or the reservoir.

However, in some cases, fully integrated systems may be employed, e.g., where the transfer conduits pass the reagents through thermally cycled zones to effect amplification. Likewise, alternative fluid transfer systems may rely upon the piercing of a bottom surface of a reservoir on a given device to allow draining of the partitions into a subsequent receptacle for amplification.

B. Mechanical Integration

In cases of mechanical integration, it will be understood that such integration will generally include automated or automatable systems for physically moving system components, such as sample plates, microfluidic devices, tubes, vials, containers, or the like, from one subsystem to another subsystem. Typically, these integrated systems will be contained within a single unified structure, such as a single casing or housing, in order to control the environments to which the various process steps, carried out by the different system components, are exposed. In some cases, different subsystem components of the overall system may be segregated from other components, in order to provide different environments for different unit operations performed within the integrated system. In such cases, pass-throughs may be provided with closures or other movable barriers to maintain environmental control as between subsystem components.

Mechanical integration systems may include robotic systems for moving sample containing components from one station to another station within the integrated system. For example, robotic systems may be employed within the integrated system to move lift and move plates from one station in a first subsystem, to another station in another subsystem.

Other mechanical integration systems may include conveyor systems, rotor table systems, inversion systems, or other translocation systems that move, e.g., a partitioning microfluidic device, tubes, or multiwall plate or plates, from one station to another station within the unified system architecture, e.g., moving a microfluidic device from its control station where partitions are generated to a subsequent processing station, such as an amplification station or fluid transfer station.

C. Examples of Integration

A number of more specific simple examples of integration of the aforementioned process components are described below.

In some cases, the up front process steps of sample extraction and purification may be integrated into the systems described herein, allowing users to input tissue, cell, or other unprocessed samples into the system in order to yield sequence data for those samples. Such systems would typically employ integrated systems for lysis of cell materials and purification of desired materials from non-desired materials, e.g., using integrated filter components, e.g., integrated into a sample vessel that could be integrated onto a microfluidic device inlet reservoir following extraction and purification. These systems again would be driven by one or more of pressure or vacuum, or in some cases, by gravitation al flow or through centrifugal driving, e.g., where sample vessels are positioned onto a rotor to drive fluid movements.

In some cases, it may be desirable to have sample nucleic acids size-selected, in order to better optimize an overall sample preparation process. In particular, it may be desirable to have one or more selected starting fragment size ranges for nucleic acid fragments that are to be partitioned, fragmented and barcoded, prior to subjecting these materials to sequencing. This is particularly useful in the context of partition-based barcoding and amplification where larger starting fragment sizes may be more desirable. Examples of available size selection systems include, e.g., the Blue Pippen® system, available from Sage Sciences (See also U.S. Pat. No. 8,361,299), that relies upon size separation through an electrophoretic gel system, to provide relatively tightly defined fragment sizes.

In accordance with the present disclosure, systems may include an integrated size selection system for generating nucleic acid fragments of selected sizes. While in some cases, these size selection components may be integrated through fluid transport systems that transport fragments into the inlet reservoirs of the fluidic components, e.g., pipetting systems, in certain cases, the size selection system may be integrated within the fluidic component itself, such that samples of varied fragment sizes may be input into the device by the user, followed by an integrated size separation process whereby selected fragment sizes may be allocated into inlet reservoirs for the fluidic components of the device.

Figure 7:
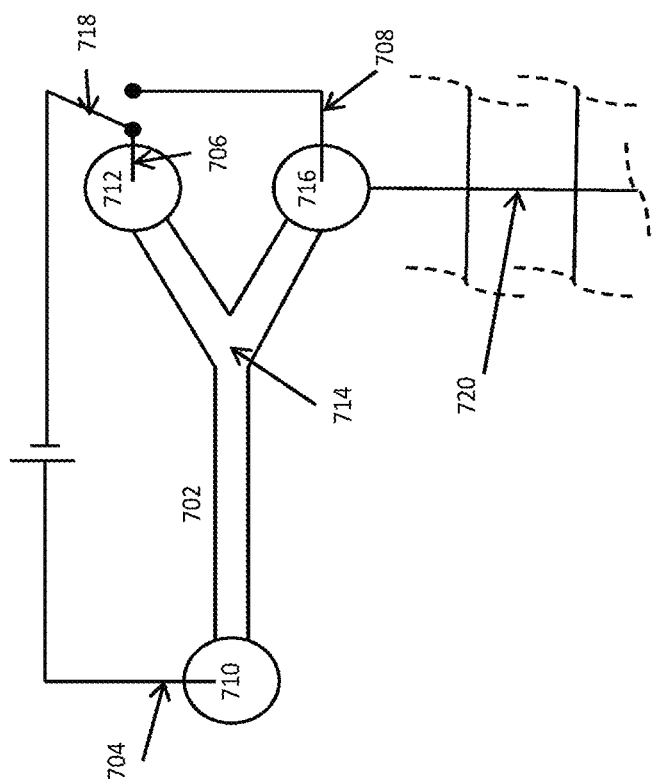
FIG. 7 schematically illustrates the integration of a nucleic acid size fragment selection component into a microfluidic partitioning component.

For example, and as shown in FIG. 7, a size selection component 700 including a capillary or separation lane 702, is integrated into a microfluidic device. An electrophoretic controller is coupled to the separation lane via electrodes 704, 706 and 708 that apply a voltage differential across the separation matrix in lane 702 in order to drive the size-based separation of nucleic acid samples that are introduced into well 710. In operation, a separation voltage differential is applied across the separation lane by applying the voltage differential between sample reservoir 710 and waste reservoir 712. At the point in the separation at which the desired fragment size enters into junction 714, the voltage differential is applied between reservoir 710 and elution reservoir 716, by actuation of switch 718. This switch of the applied voltage differential then drives the desired fragment size into the elution reservoir 716, which also doubles as the sample inlet reservoir for the microfluidic device, e.g., reservoir 232 in FIG. 2. Once sufficient time has passed for direction of the desired fragment into reservoir 716, the voltage may again be switched as between reservoir 710 and waste reservoir 712.

Upon completion of the separation, fragments that have been driven into the sample elution reservoir/sample inlet reservoir, may then be introduced into their respective microfluidic partitioning channel network, e.g., channel network 720, for allocation into partitions for subsequent processing. As will be appreciated, in cases where an electrophoretic separation component is included within the system, e.g., whether integrated into the microfluidic device component or separate from it, the systems described herein will optionally include an electrophoretic controller system that delivers appropriate voltage differentials to the associated electrodes that are positioned in electrical contact with the content of the relevant reservoirs. Such systems will typically include current or voltage sources, along with controllers for delivering desired voltages to specified electrodes at desired times, as well as actuation of integrated switches. These controller systems, either alone, or as a component of the overall system controller, will typically include the appropriate programming to apply voltages and activate switches to drive electrophoresis of sample fragments in accordance with a desired profile.

As will be appreciated, a single microfluidic device may include multiple partitioning channel networks, and as such, may also include multiple size separation components integrated therein as well. These size separation components may drive a similar or identical size separation process in each of the different components, e.g., to provide the same or similar sized fragments to each different partitioning channel network. Alternatively, the different size separation components may drive a different size selection, e.g., to provide different sized fragments to the different partitioning networks. This may be achieved through the inclusion of gel matrices having different porosity, e.g., to affect different separation profiles, or it may be achieved by providing different voltage profiles or switching profiles to the electrophoretic drivers of the system.

As will be appreciated, for microfluidic devices that include multiple parallel arranged partitioning channel networks, multiple separation channels may be provided; each coupled at an elution zone or reservoir that operates as or is coupled to a different inlet reservoir for the partition generating fluidic network. In operation, a plurality of different separation channel components maybe provided integrated into a microfluidic device. The separation channels again are mated with or include associated electrodes for driving electrophoresis of nucleic acids or other macromolecular sample components, through a gel matrix within the separation channels. Each of the different separation channels may be configured to provide the same or differing levels of separation, e.g., resulting in larger or smaller eluted fragments into the elution zone/inlet reservoir of each of the different partitioning channel networks. In cases where the separation channels provide different separation, each of the different channel networks would be used to partition sample fragments of a selected different size, with the resulting partitioned fragments being recovered for each channel network in a different outlet or recovery reservoir, respectively.

3. Amplification

In some cases, the systems include integration of one or more of the amplification process components, e.g., steps 610 and 612, into the overall instrument system. In particular, as will be appreciated, this integration may be as simple as incorporating a temperature control system within thermal communication with the product reservoir on the fluidic component of the system, e.g., reservoir 238 in FIG. 2, such that the contents of the reservoir may be thermally cycled to allow priming, extension, melting and re-priming of the sample nucleic acids within the partitions by the primer/barcode oligonucleotides in order to create the overlapping primer sequences template off of the original sample fragment. Again, such temperature control systems may include heating elements thermally coupled to a portion of the fluidic component so as to thermally cycle the contents of the outlet reservoir.

Alternatively, the integration of the amplification system may provide for fluid transfer from the outlet reservoir of the fluidic component to an amplification reservoir that is positioned in thermal contact with the above described temperature control system, e.g., in a temperature controlled thermal cycler block, within the instrument, that is controlled to provide the desired thermal cycling profile to the contents taken from the outlet reservoir. As described above, this fluid transfer system may include, e.g., a pipetting system for drawing the partitioned components out of the outlet reservoir of the microfluidic device and depositing them into a separate reservoir, e.g., in a well of a multiwall plate, or the like. In another alternative configuration, fluid transfer between the microfluidic device and the amplification reservoir may be directed by gravity or pressure driven flow that is actuated by piercing a lower barrier to the outlet reservoir of the microfluidic device, allowing the generated partitions to drain or flow into a separate reservoir below the microfluidic device that is in thermal communication with a temperature control system that operates to thermally cycle the resultant partitions through desired amplification thermal profiles.

In a particular example, and with reference to the nucleic acid analysis workflow set forth above, the generated partitions from step 608 may be removed from the fluidics component by an integrated fluid transfer system, e.g., pipettors, that withdraw the created partitions form, e.g., reservoir 238 of FIG. 2, and transport those partitions to an integrated thermal cycling system in order to conduct an amplification reaction on the materials contained within those partitions. Typically, the reagents necessary for this initial amplification reaction (shown at step 610, in FIG. 6), will be co-partitioned in the partitions. In many cases, the integrated thermal cycling systems may comprise separate reagent tubes disposed within thermal cycling blocks within the instrument, in order to prevent sample to sample cross contamination. In such cases, the fluid transport systems will withdraw the partitioned materials from the outlet reservoir and dispense them into the tubes associated with the amplification system.

4. Size Selection of Amplification Products

Following amplification and barcoding step 610, the partitioned reagents are then pooled by breaking the emulsion, and subjected to additional processing. Again, this may be handled through integrated fluid transfer systems that may introduce reagents into the wells or tubes in which the sample materials are contained, or by transferring those components to other tubes in which such additional reagents are located. In some cases, mechanical components may also be included within the system to assist in breaking emulsions, e.g., through vortexing of sample vessels, plates, or the like. Such vortexing may again be provided within a set station within the integrated system. In some cases, this additional processing may include a size selection step in order to provide sequenceable fragments of a desired length.

5. Additional Processing and Sequencing

Following further amplification, it may be desirable to include additional clean up steps to remove any unwanted proteins or other materials that may interfere with a sequencing operation. In such cases, solid phase DNA separation techniques are particularly useful, including, the use of nucleic acid affinity beads, such as SPRI beads, e.g., Ampure® beads available from Beckman-Coulter, for purification of nucleic acids away from other components in fluid mixtures. Again, as with any of the various unit operations described herein, this step may be automated and integrated within the overall integrated instrument system.

In addition to integration of the various upstream processes of sequencing within an integrated system, in some cases, these integrated systems may also include an integrated sequencer system. In particular, in some cases, a single integrated system may include one, two, three or more of the unit process subsystems described above, integrated with a sequencing subsystem, whereby prepared sequencing libraries may be automatically transferred to the sequencing system for sequence analysis. In such cases, following a final pre-sequencing process, the prepared sequencing library may be transferred by an integrated fluid transfer system, to the sample inlet of a sequencing flow cell or other sequencing interface. The sequencing flow cell is then processed in the same manner as non-integrated sequencing samples, but without user intervention between library preparation and sequencing.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A device configured to facilitate sample processing, comprising:
   a holder configured to receive a microfluidic device, wherein said holder is coupled to a rotatable body, wherein said rotatable body is configured to alternate between a closed configuration and an open configuration, wherein said microfluidic device comprises a plurality of channel networks for partitioning a sample into a plurality of partitioned samples, said plurality of channel networks being connected to a plurality of inlet and outlet reservoirs, and
   wherein (i) in said closed configuration, said holder is configured to allow pressure communication between said plurality of inlet and outlet reservoirs and an interfaced instrument, and (ii) in said open configuration, said holder is configured to permit said microfluidic device to be inserted into or removed from said holder.

2. The device of claim 1, further comprising a gasket coupled to said rotatable body.

3. The device of claim 2, wherein said gasket is removable from said rotatable body.

4. The device of claim 2, wherein said gasket comprises securing features configured to mate with complementary features on said rotatable body.

5. The device of claim 2, wherein said gasket comprises a plurality of apertures configured to be aligned with an inlet reservoir or an outlet reservoir of a channel network of said plurality of channel networks when said microfluidic device is secured in said holder and said rotatable body is in said closed configuration.

6. The device of claim 1, wherein said plurality of channel networks are substantially parallel to one another when said microfluidic device is secured in said holder.

7. The device of claim 1, wherein a gasket is coupled to said microfluidic device.

8. The device of claim 7, wherein said gasket is removable from said microfluidic device.

9. The device of claim 1, wherein a channel network of said plurality of channel networks comprises a plurality of interconnected fluid channels connected at a channel junction, wherein said channel junction is configured to combine a first fluid containing said sample with a stream of a second fluid immiscible with said first fluid, to partition said sample into discrete droplets within said second fluid, to thereby provide said partitioned samples within said discrete droplets, which discrete droplets are stored in an outlet reservoir of said plurality of outlet reservoirs or a storage vessel.

10. The device of claim 9, wherein said plurality of interconnected fluid channels is part of a monolithic microfluidic structure having intersecting fluid channels.

11. The device of claim 1, wherein in said open configuration, said rotatable body is configured to support said holder against a surface.

12. The device of claim 1, further comprising at least one monitoring component configured to interface with a channel network of said plurality of channel networks when said microfluidic device is received in said holder, wherein said at least one monitoring component is configured to observe or monitor one or more characteristics or properties of said at least one of said plurality of channel networks and fluids flowing therein.

13. The device of claim 12, wherein a monitoring component of said at least one monitoring component is selected from the group consisting of a temperature sensor, a pressure sensor, and a humidity sensor.

14. The device of claim 1, wherein at least one channel of said channel network comprises a channel segment that widens, wherein said channel segment is configured to control flow by breaking capillary forces acting to draw a fluid into said at least one channel.

15. The device of claim 1, wherein at least one channel of said channel network comprises a passive check valve.

16. The device of claim 1, wherein a channel network of said plurality of channel networks comprises:
   a first channel segment fluidly connected to a source of barcode reagents;
   a second channel segment fluidly connected to a source of said sample, wherein said first channel segment and said second channel segment are fluidly connected to a first channel junction;
   a third channel segment and a fourth channel segment, wherein said third channel segment is fluidly connected to said first channel junction, wherein said fourth channel segment is fluidly connected to a source of partitioning fluid, and wherein said third channel segment and said fourth channel segment are fluidly connected to a second channel junction; and
   a fifth channel segment fluidly connected to said second channel junction,
   wherein said instrument is configured to interface with said channel network to (i) drive flow of said barcode reagents and said sample into said first channel junction to form a reagent mixture comprising said barcode reagents and said sample in said third channel segment, and (ii) drive flow of said reagent mixture and said partitioning fluid into said second channel junction to form droplets comprising said reagent mixture in a stream of partitioning fluid within said fifth channel segment.

17. The device of claim 1, wherein in said open configuration, said holder is configured to allow said microfluidic device to stand at a desired angle to facilitate recovery of a partitioned sample of said plurality of partitioned samples from an outlet reservoir of said plurality of inlet and outlet reservoirs.

18. The device of claim 17, wherein said desired angle is an angle in a range from 20 degrees to 70 degrees.

19. The device of claim 18, wherein said desired angle is in a range from 40 degrees to about 50 degrees.

20. The device of claim 19, wherein said desired angle is about 45 degrees.

21. The device of claim 1, wherein said instrument comprises:
   (a) a retractable tray supporting and seating said holder, and slideable into and out of said instrument;
   (b) a depressible manifold assembly configured to be actuated and lowered to the microfluidic device and to sealaby interface with the plurality of inlet and outlet reservoirs, when said microfluidic device is received in said holder;
   (c) at least one fluid drive component configured to apply a pressure differential between the plurality of inlet and outlet reservoirs when said microfluidic device is received in said holder; and
   (d) a controller configured to operate at least one fluid drive component to apply said pressure differential depending on a mode of operation or according to preprogrammed instructions.

* * * * *